(12) United States Patent
Belalcazar

(10) Patent No.: US 10,201,474 B2
(45) Date of Patent: Feb. 12, 2019

(54) METHOD AND APPARATUS FOR IMPROVED VENTILATION AND CARDIO-PULMONARY RESUSCITATION

(71) Applicant: Hugo Andres Belalcazar, Minneapolis, MN (US)

(72) Inventor: Hugo Andres Belalcazar, Minneapolis, MN (US)

( * ) Notice: Subject to any disclaimer, the term of this patent is extended or adjusted under 35 U.S.C. 154(b) by 952 days.

(21) Appl. No.: 14/705,702

(22) Filed: May 6, 2015

(65) Prior Publication Data

US 2015/0231028 A1 Aug. 20, 2015

Related U.S. Application Data

(63) Continuation-in-part of application No. 13/751,121, filed on Jan. 27, 2013, now abandoned, and a
(Continued)

(51) Int. Cl.
*A61H 31/00* (2006.01)
*A61M 16/10* (2006.01)
(Continued)

(52) U.S. Cl.
CPC ......... *A61H 31/007* (2013.01); *A61H 31/006* (2013.01); *A61M 16/06* (2013.01); *A61M 16/0677* (2014.02); *A61M 16/085* (2014.02); *A61M 16/0858* (2014.02); *A61M 16/10* (2013.01); *A61M 16/1005* (2014.02);
(Continued)

(58) Field of Classification Search
CPC .............. A61H 31/00–31/02; A61H 2031/025
See application file for complete search history.

(56) References Cited

U.S. PATENT DOCUMENTS 4,397,306 A * 8/1983 Weisfeldt ............. A61H 9/0078
601/41
6,155,257 A * 12/2000 Lurie ................... A61H 31/005
128/204.18
(Continued)

OTHER PUBLICATIONS

"Arterial blood gases with 700 ml tidal volumes during out-of-hospital CPR" by Dorph, Wik and Steen, published in the journal Resuscitation, vol. 61 of 2004, pp. 23-27.

*Primary Examiner* — Rachel T Sippel

(57) ABSTRACT

A cardio-pulmonary resuscitation apparatus and method that provides mechanical compressions and oxygen delivery to a patient. The delivered oxygen quantity is based on the anterior to posterior distance of the patient. Tidal volumes of the delivered oxygen are calculated from the anterior to posterior distance. The compressions and oxygen may be delivered in sequences that enhance the circulation of the patient. The compressions may be sensed by a sensor to effect such sequences. Oxygen delivered based on the anterior to posterior distance may be further adjusted by airway pressure. Embodiments may include a tube with lumens to deliver oxygen, monitor airway pressure, and contain wires to activate the airway valve and monitor airway pressure. Embodiments may also include a carbon dioxide sensor and may use two tidal volumes, the larger one to sample the end tidal carbon dioxide. Also included in some embodiments is a safety relief valve.

25 Claims, 20 Drawing Sheets

Related U.S. Application Data continuation-in-part of application No. 13/733,887, filed on Jan. 4, 2013, now abandoned, and a continuation-in-part of application No. 13/674,029, filed on Nov. 10, 2012, now Pat. No. 9,265,691, and a continuation-in-part of application No. 13/070,504, filed on Mar. 24, 2011, now Pat. No. 8,435,193, and a continuation-in-part of application No. 12/558,437, filed on Sep. 11, 2009, now Pat. No. 8,366,645.

(60) Provisional application No. 61/730,944, filed on Nov. 28, 2012, provisional application No. 61/557,918, filed on Nov. 10, 2011, provisional application No. 61/316,979, filed on Mar. 24, 2010, provisional application No. 61/096,316, filed on Sep. 12, 2008.

(51) Int. Cl.
*A61M 16/20* (2006.01)
*A61M 16/06* (2006.01)
*A61M 16/08* (2006.01)
*A61M 16/00* (2006.01)

(52) U.S. Cl.
CPC .......... *A61M 16/20* (2013.01); *A61M 16/202* (2014.02); *A61H 31/004* (2013.01); *A61H 2201/0173* (2013.01); *A61H 2201/1207* (2013.01); *A61H 2201/1246* (2013.01); *A61H 2201/5056* (2013.01); *A61H 2201/5064* (2013.01); *A61M 16/0069* (2014.02); *A61M 2016/0027* (2013.01); *A61M 2202/0208* (2013.01); *A61M 2205/056* (2013.01); *A61M 2205/332* (2013.01); *A61M 2230/432* (2013.01)

(56) References Cited

U.S. PATENT DOCUMENTS

| | | | |
|---|---|---|---|
| 8,408,207 B2* | 4/2013 | Steen | A61M 16/042 128/204.23 |
| 2014/0031729 A1* | 1/2014 | Belalcazar | A61H 31/00 601/41 |

* cited by examiner

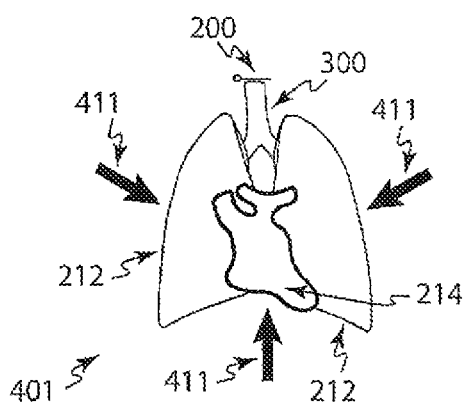
FIG. 4A
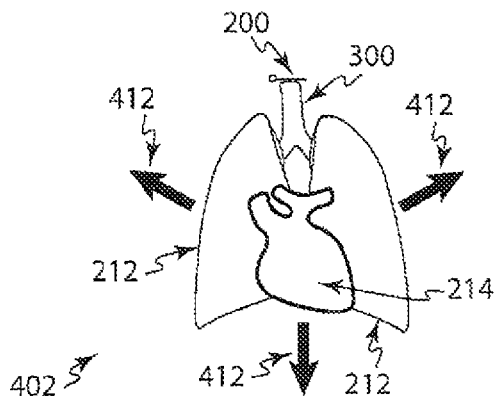
FIG. 4B
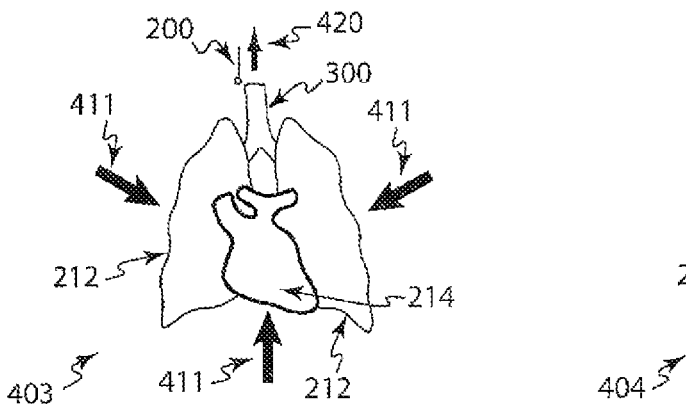
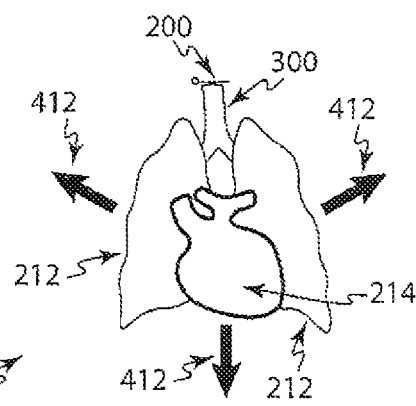
FIG. 4C
FIG. 4D
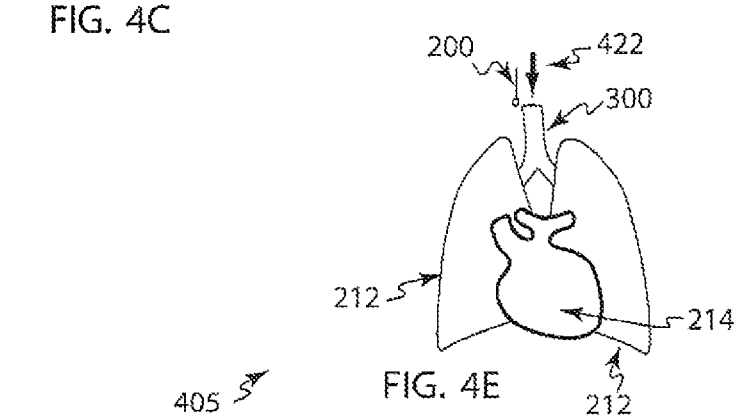
FIG. 4E

952

954

956

METHOD AND APPARATUS FOR IMPROVED VENTILATION AND CARDIO-PULMONARY RESUSCITATION

CROSS REFERENCE TO RELATED APPLICATIONS

This patent application is a continuation-in-part of patent application Ser. No. 13/751,121 filed on 2013 Jan. 27, which is a continuation-in-part of Ser. No. 13/733,887 filed on 2013 Jan. 4, which is a continuation-in-part of patent application Ser. No. 13/674,029, filed on 2012 Nov. 10, which is a continuation-in-part of patent application Ser. No. 13/070,504, filed on 2011 Mar. 24, which is a continuation-in-part of patent application Ser. No. 12/558,437, filed on 2009 Sep. 11. This patent application is further a continuation-in-part of patent application Ser. Nos. 13/674,029; 13/070,504; and Ser. No. 12/558,437. Patent application Ser. No. 13/733,887 claims the benefit of provisional patent application 61/730,944, filed 2012 Nov. 28, and also claims the benefit of patent application Ser. No. 13/674,029 filed on 2012 Nov. 10. Patent application Ser. No. 13/674,029 claims the benefit of provisional patent application 61/557,918, filed 2011 Nov. 10, and also claims the benefit of patent application Ser. No. 13/070,504, filed on 2011 Mar. 24, which claims the benefit of provisional patent application 61/316,979 filed 2010 Mar. 24, and also claims the benefit of patent application Ser. No. 12/558,437 filed 2009 Sep. 11, which claims the benefit of provisional patent application 61/096,316 filed 2008 Sep. 12. Each of the patent application Ser. Nos. 12/558,437, 13/070,504, 13/674,029, 13/733,887, and 13/751,121 and the provisional patent applications 61/730,944, 61/096,316, 61/316,979, and 61/557,918 are incorporated herein by reference.

FEDERALLY SPONSORED RESEARCH

None.

SEQUENCE LISTING

None.

FIELD OF THE INVENTION

The present invention relates generally to apparatuses and methods used in ventilation and cardio-pulmonary resuscitation.

BACKGROUND

This invention relates to the field of cardiopulmonary resuscitation. In particular, the invention provides improved devices and methods for enhancing blood circulation in patients undergoing cardiopulmonary resuscitation (hereon abbreviated as CPR). Such procedure is applied, for example, when cardiac arrest is present. In these situations, the heart ceases to pump blood out of the heart. To obtain some circulation until the normal pumping action of the heart can be restored, manual compressions are conventionally applied on the chest of the supine patient. The compressions on the chest may be alternated with brief periods of forced breathing into the patient, for example, by mouth to mouth ventilation. Alternatively, a ventilation bag with facemask or tracheal tube may be used to achieve the same effect. The American Heart Association publishes guidelines on CPR procedures. For example, the "2005 American Heart Association Guidelines for Cardiopulmonary Resuscitation and Emergency Cardiovascular Care", published in the Circulation journal, give a good overview of the subject of CPR.

While manual compressions are partially effective in providing circulation to the patient, it is not a perfect method. The manual compressions applied on the chest attempt to squeeze the heart and major vascular structures to eject blood into the extrathoracic arterial circulation. However, the rib cage provides an obstacle to achieve effective squeezing of the heart and vascular structures. The rib cage, in fact, spatially protects the internal organs including the heart from external forces. As a result, the physical frame forming the rib cage attenuates the amount of squeezing on the heart obtained by external compressions on the chest, by distributing the force across entire chest and rib cage.

Furthermore, when a rescuer provides CPR and compresses the chest of the patient, the heart only experiences a partial squeeze, because soft tissues surround the heart and mediastinum. Namely, the soft tissues are the lungs on the sides of the mediastinum, and inferiorly, the soft tissues of the upper abdomen. As the external compression is delivered, the heart deforms and expands part of its volume into the surrounding soft tissues. This expansion creates inefficiencies in squeezing the heart during CPR. It would be desirable to impede that lateral expansion into soft tissues so that a more effective cardiac squeeze is achieved. One such method to effectively accomplish such lateral support is open chest cardiac massage, in which clinicians manually squeeze the heart with their hands. In this case the squeeze of the heart is delivered around most of the heart's perimeter, not just the front and back as in traditional CPR. The squeeze is therefore very effective, but it of course requires a very invasive surgery to expose the heart, and is thus not amenable to typical CPR and first aid situations. In any case, the point emphasized here is the inefficiency of the squeeze of the heart due to its laterally surrounding soft tissues and its protective rib cage, as provided by conventional CPR methods.

In an effort to alleviate some of the above shortcomings, and to enhance circulation during CPR, several devices have been proposed in prior art. For example, U.S. Pat. No. 5,551,420 to Lurie describes a special valve coupled to the airway of the patient, such that the flow of air into the patient's lungs is restricted during the chest decompression phase of CPR. The valve's restriction of air inflow into the patient's lungs, in combination with the natural elastic recoil of the chest after a compression, causes a negative intrathoracic pressure. This vacuum helps draw venous blood from the body into the thorax prior to the next chest compression, thereby better priming the heart pump with enhanced filling. As a result, more blood is in the heart when the next compression occurs, and therefore, more blood is ejected, obtaining enhanced circulation.

In the above cited '420 patent, Lurie also mentions the use of positive pressure, by implementing a restriction to outflow of air from the patient's lungs during the compression phase of CPR. It can be appreciated that if the airway is restricted to outflow, greater intrathoracic pressure will be obtained during a compression step of CPR. Such enhanced pressure will help develop a more efficient ejection of blood from the heart. This addresses the inefficiency of cardiac expansion of the heart into surrounding soft tissues during external compression. Because the lungs cannot readily evacuate their air due to the outflow restriction, the heart is laterally impeded from expanding into the lung spaces. This contributes to a more effective squeeze of the heart when applying external compression to the front of the chest.

The prior art however does not describe a sequence, nor a device to provide it, that would combine optimized positive and negative pressures. Furthermore, when passive decompression CPR is used according to the known art, there is a disadvantage when providing inflow air-resistance during more than a few compression cycles. The distinction of active and passive decompression in CPR merits explanation at this point. By passive decompression CPR it is understood that no active devices are used to expand the chest after each compression step, for example, by using suction cups on the skin to pull and expand the chest. In passive decompression CPR, the chest is allowed to naturally and elastically recover in shape after each compression. The discussion below, and for the rest of this document, is framed in the context of passive decompression CPR, which is the most commonly used method.

Describing the disadvantage in more detail, when using the known inflow restriction devices, there will be less air exchange occurring than there would be if no air restriction was present. In consequence, there will be less air volume present in the lungs just prior to the compression phase of CPR. In other words, after a few compression-decompression cycles, the patient's chest will hold less air volume at the end of the chest decompression phase, due to the impediment presented by the special valve, which restricts the filling of the lungs. Air is easily ejected from the lungs with chest compression and an open airway, but not so easily inhaled through the restrictive valve. Therefore, the chest will not inflate fully to its natural relaxed state. This volume deficiency will be greater if the cracking pressure is set to a higher value on the inflow restriction valve. The cracking pressure is the pressure at which the valve will open to allow air inflow to the lungs, when the valve is subjected to negative pressure at the patient airway side. It can also be understood as the amount of inflow resistance. It must be properly set for the particular patient, as a child, for instance, may have different negative pressure requirements than a large adult.

The extreme situation of lung air volume reduction occurs with a very high cracking pressure: the air inflow is completely occluded when the chest attempts to expand during the decompression phase of CPR, and no new air enters the chest. Notice that this happens even the though the elastic recoil of the chest creates a relatively high vacuum to draw blood to the heart from the periphery. So while blood is adequately drawn into the chest by vacuum, it is done at the expense of air intake.

The disadvantage noted above has two implications: first, barring manually delivered ventilations, which defeat the negative pressure advantages, there is less respiratory gas exchange with the outside atmosphere than in traditional open airway CPR, so oxygen and carbon dioxide transport is negatively affected. Second, if a device or method were to simply combine vacuum with a positive pressure technique as described earlier (restricting air outflow during chest compression to enhance ventricular blood ejection), it will be less effective. This inefficiency of the compression phase of any such simple combination has not been noted in the prior art. The inefficiency occurs because, with the reduced volume of lung air present at the beginning of the chest compression, the heart and major vessels can more easily deform and expand into the less inflated lung space. In contrast, if the precise states of the lungs and heart were taken into account, for example, if the lungs were instead optimally full of air, and the outflow of air restricted during chest compression, the squeeze on the heart would be enhanced, as inflated lungs present a better lateral obstruction to the heart, than do deflated lungs. Such is one of the objectives of the invention. Similarly, if a vacuum were to be applied without regard to the prior states of the cardiopulmonary system, the benefit of the negative pressure may not be optimal. Therefore, an optimized combination of vacuum and positive pressures is sought in order to further enhance cardio pulmonary circulation. Further, it would be desirable to accomplish such combination without significantly impairing ventilation of the patient. What is also needed is a device and method that optimally provides both negative and positive intrathoracic pressures to enhance circulation during CPR, but does so while maintaining a degree of gas exchange that does not substantially defeat the assistive thoracic pressures.

The invention embodiments described in this document address these needed characteristics, while offering further advantages, and will therefore provide for enhanced CPR devices and methods.

SUMMARY

Provided is an apparatus having a sealing means to control an airway of a patient, the patient further having lungs, a chest, and an anterior to posterior distance. The apparatus further includes an airway valve that in combination with the sealing means is configured to open and close the airway. Also included are means to actuate the airway valve, an oxygen source to deliver oxygen to the patient, and means to deliver mechanical compressions to the patient's chest. The apparatus includes a control unit coupled to the airway valve actuating means, oxygen valve actuator, and mechanical compression delivery means. Moreover, the control unit is configured to actuate the airway valve, mechanical compression delivery means, and oxygen valve to deliver oxygen quantities based on the patient's anterior to posterior distance. The apparatus may measure the anterior to posterior distance. Furthermore, the control unit may be configured to calculate a tidal volume from the anterior to posterior distance. In addition, the control unit may be further configured to actuate the airway valve, mechanical compression delivery means, and oxygen valve to effect a predetermined state of sequences, potentially in combination with sensor means to sense compressions on the patient's chest.

Also provided is an apparatus including sealing means to control the airway of a patient, the patient also having a chest, lungs, airway pressure, and anterior to posterior distance. The apparatus may further include an airway valve that in combination with the sealing means is configured to open and close the airway. Also included are means to actuate the airway valve, an oxygen source to deliver oxygen to the patient, an oxygen valve to control oxygen flow, an oxygen valve actuator, means to deliver mechanical compressions to the chest and means to monitor the airway pressure. Also included may be a control unit coupled to the airway valve actuating means, oxygen valve actuator, airway pressure monitoring means, and mechanical compression delivery means. The control unit may be configured to actuate the airway valve, mechanical compression delivery means and oxygen valve to deliver oxygen quantities based on the anterior to posterior distance. The control unit may further be configured to automatically adjust the quantities based on the airway pressure.

The apparatus may further comprise at least one tube having a first lumen and a second lumen. The first lumen may provide oxygen flow to the patient, while the second lumen may comprise means to monitor the air way pressure. The second lumen may further comprise wires wherein the wires are configured to perform functions consisting of airway valve activation conduction, communication of airway pressure, carry electric signals to a pressure transducer, and combinations thereof. In addition, the control unit maybe further configured to actuate the airway valve, mechanical compression delivery means, and oxygen valve to effect a predetermined state of sequences, potentially in combination with sensor means to sense compressions on the patient's chest.

In another aspect of the invention, an apparatus is provided having sealing means to control the airway of a patient. Moreover, the apparatus includes an airway valve that in combination with the sealing means is configured to open and close the airway. The apparatus may further include means to actuate the airway valve, an oxygen source to deliver oxygen to the patient, and oxygen valve to control oxygen flow, and an oxygen valve actuator. Also included may be means to deliver mechanical compression to the patient's chest. The apparatus may further include means to monitor exhaled carbon dioxide of the patient. A control unit may be included which is coupled to the airway valve actuating means, oxygen valve actuator, mechanical compression delivery means, and carbon dioxide monitoring means. The control unit may be configured to carry out a predetermined sequence of chest compressions and oxygen ventilation, with the oxygen ventilation having either a first tidal volume or a larger second tidal volume. The means to monitor exhaled carbon dioxide of the patient may use the larger second tidal volume to monitor the exhaled carbon dioxide. In one embodiment the larger second tidal volume may be delivered no more often than once every fifteen seconds. In another embodiment, the larger second tidal volume may be delivered at intervals between once every fifteen seconds to once every minute.

Also provided is a cardio-pulmonary resuscitation apparatus comprising an airway valve. The airway valve may include means to provide a safety relief when a pressure within the valve is great enough to actuate the safety relief, the safety relief comprising a spring and a sealing surface wherein the pressure presses against the sealing surface to actuate the spring. The spring may have a spring constant corresponding to a relief pressure less than forty centimeters of water. The apparatus may further provide sealing means to control the airway of the patient. The airway valve may further include an oxygen port connected to an oxygen source having an oxygen valve and means to actuate the oxygen valve. The oxygen port may be angled toward the airway. The airway valve may further include a pressure sampling port for monitoring a pressure of the airway by an airway pressure monitoring means and a carbon dioxide sampling port for monitoring exhaled carbon dioxide of the patient by a carbon dioxide monitoring means. Further included may be means to actuate the airway valve and means to deliver mechanical compressions to the chest of the patient. Also included may be a control unit coupled to the airway valve actuating means, oxygen valve actuator, airway pressure monitoring means, carbon dioxide monitoring means, and mechanical compression delivery means. In one embodiment, the relief pressure may be between ten centimeters of water and forty centimeters of water.

BRIEF DESCRIPTION OF THE DRAWINGS

FIG. 4A shows the first state in the sequence of operative states of the cardio-pulmonary system and the airway valve, achieved with the invention.

FIG. 4B shows the second state in the sequence of operative states of the cardio-pulmonary system and the airway valve, achieved with the invention.

FIG. 4C shows the third state in the sequence of operative states of the cardio-pulmonary system and the airway valve, achieved with the invention.

FIG. 4D shows the fourth state in the sequence of operative states of the cardio-pulmonary system and the airway valve, achieved with the invention.

FIG. 4E shows the fifth state in the sequence of operative states of the cardio-pulmonary system and the airway valve, achieved with the invention.

DETAILED DESCRIPTION

Figure 1:
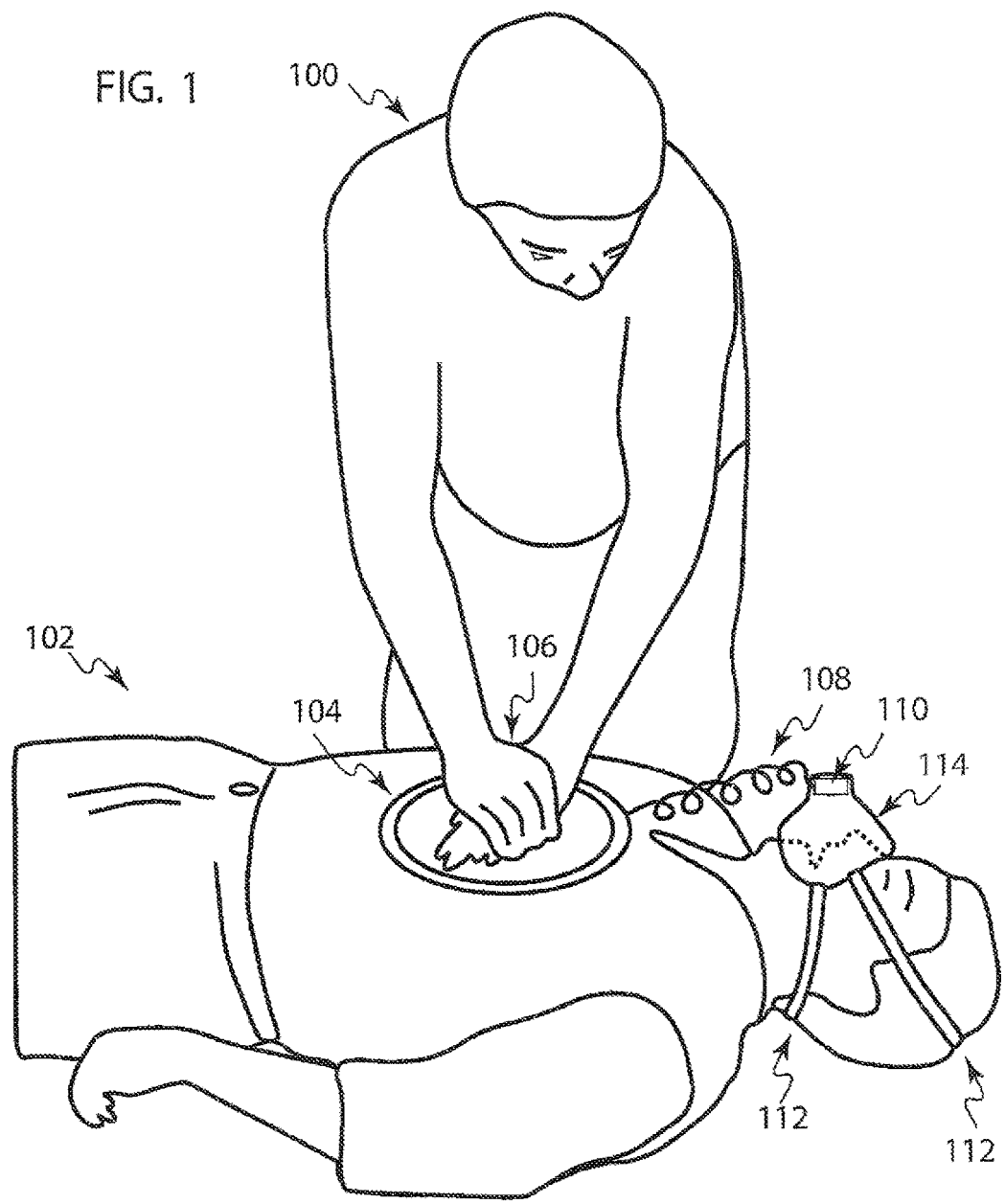
FIG. 1 shows an embodiment of the invention being used to administer CPR on a patient.

FIG. 1 shows a rescuer 100 and a patient 102 who is undergoing cardio-pulmonary resuscitation (CPR). It is noted here that the term CPR also includes the mode of resuscitation where no ventilations, (by mouth-to-mouth, bag, or otherwise), are given to the patient. For example, cardio-cerebral resuscitation (CCR), is understood throughout this document to be also included when the term CPR is used. As is well known in the field, rescuer 100 uses his/her hands 106 to press against the chest of patient 102. In accordance to one embodiment of the invention, a compression sensor 104 is placed on the chest of the patient. Rescuer 100 delivers the chest compressions through compression sensor 104 to the chest of the patient. Compression sensor 104 is sized and formed, preferably in a flattened manner as shown in FIG. 1, to be placed on the chest of the patient 102. It is constructed preferably of a material that will not slide easily off the patient 102. Suitable materials include, but are not limited to, rubber, latex, silicone, and the like. Compression sensor 104 operates to receive the force of the hands 106 of the rescuer 100, and transmit it to the patient 102, in a manner consistent with conventional CPR. In order to accomplish the function of sensing of compressions and decompressions, sensor 104 may include a switch operable by the force delivered by the rescuer 100. When the hands 106 press downward and deliver a compression to the chest of patient 102, the switch may close an electric circuit, signaling the beginning of compression. When the force on the chest of the patient is relieved during the decompression phase of CPR, the switch opens, signaling the beginning of said phase. Other forms of sensing the force of the rescuer 100 on the patient 102 may be used, as is known conventionally in the field of electrical and mechanical engineering. For example, sensor 104 may be constructed using a capacitive design, where two conductive plates or membranes separated by a dielectric are used. A separate electric circuit may be used to sense the change in capacitance and indicate a compression. Said switch, conductive plates, or conductive membranes constitute sensor means to sense compressions on the chest of the patient. Other similar means can be used, including magnetic, resistive, pneumatic, or others as known in the electrical and mechanical arts. In the pneumatic instance, sensor 104 can be constructed as a flattened rubber bellows. As such, it expels air every time it is compressed. Such air can be conducted by a hose conductor 108 to the facial mask, to be used as a synchronizing signal, as will be further described below, in accordance to this invention. The sensor 104 embodied with a bellows may also include a one way intake air valve, and a recoil spring, to achieve re-inflation after each compression.

Describing further elements and function of the invention, the information or signal of compression or decompression given by hands 106 of the rescuer 100 is transmitted via a conductor 108 to an air flow control assembly 110 that forms part of a facial mask 114. Facial mask 114 is coupled to the face of the patient 102 with straps 112 so as to achieve a near or complete air seal. In this manner, air flow control assembly 110 either opens or occludes in a complete or nearly complete manner the airway of the patient, thereby exclusively controlling the ventilation and airflow to and from the lungs of the patient 102. Thus facial mask 114 constitutes a sealing means to control the airway of the patient. Using an inventive and advantageous sequence synchronized with the chest compressions, said patient air flow is controlled so as to provide enhanced cardiopulmonary circulation of blood. Such inventive sequence will be further described later in this document.

Simple electrical wires can realize conductor 108 of FIG. 1. In the embodiment of sensor 104 that includes an electric switch, a pair of electric wire conductors are coupled to the switch, and therefore convey the state of the switch to air flow control assembly 110. Alternatively, sensor 104 is capacitive, and conductor 108 could include at least two wires to couple the capacitance to airflow control assembly 110. Alternatively, conductor 108 can be a semi-rigid rubber or plastic hose that conveys air or liquid pressure squeezed from a similarly filled bellows sensor 104. As an even further alternative, conductor 108 can be eliminated if wireless methods of signal transmission from sensor 104 to airflow control assembly 110 are used. As will be apparent to those skilled in basic techniques of electrical and mechanical engineering, alternative sensor and signal conduction devices are possible without departing from the spirit of this part of the invention. That is, to detect when chest compression and decompressions occur, and to deliver such signal to the airflow control assembly 110.

In one embodiment, conductor 108 may also include electric conductors to supply electrical power to airflow control assembly 110, when an energy source, such as a battery is used. Such battery may be included in sensor 104, or further distally coupled to it via other conductors (not shown) that could lie beside the patient 102. Alternative battery sources and arrangements are easily apparent to those skilled in the electrical arts, and may be included within various components of the invention, without departing from its scope.

Figure 2:
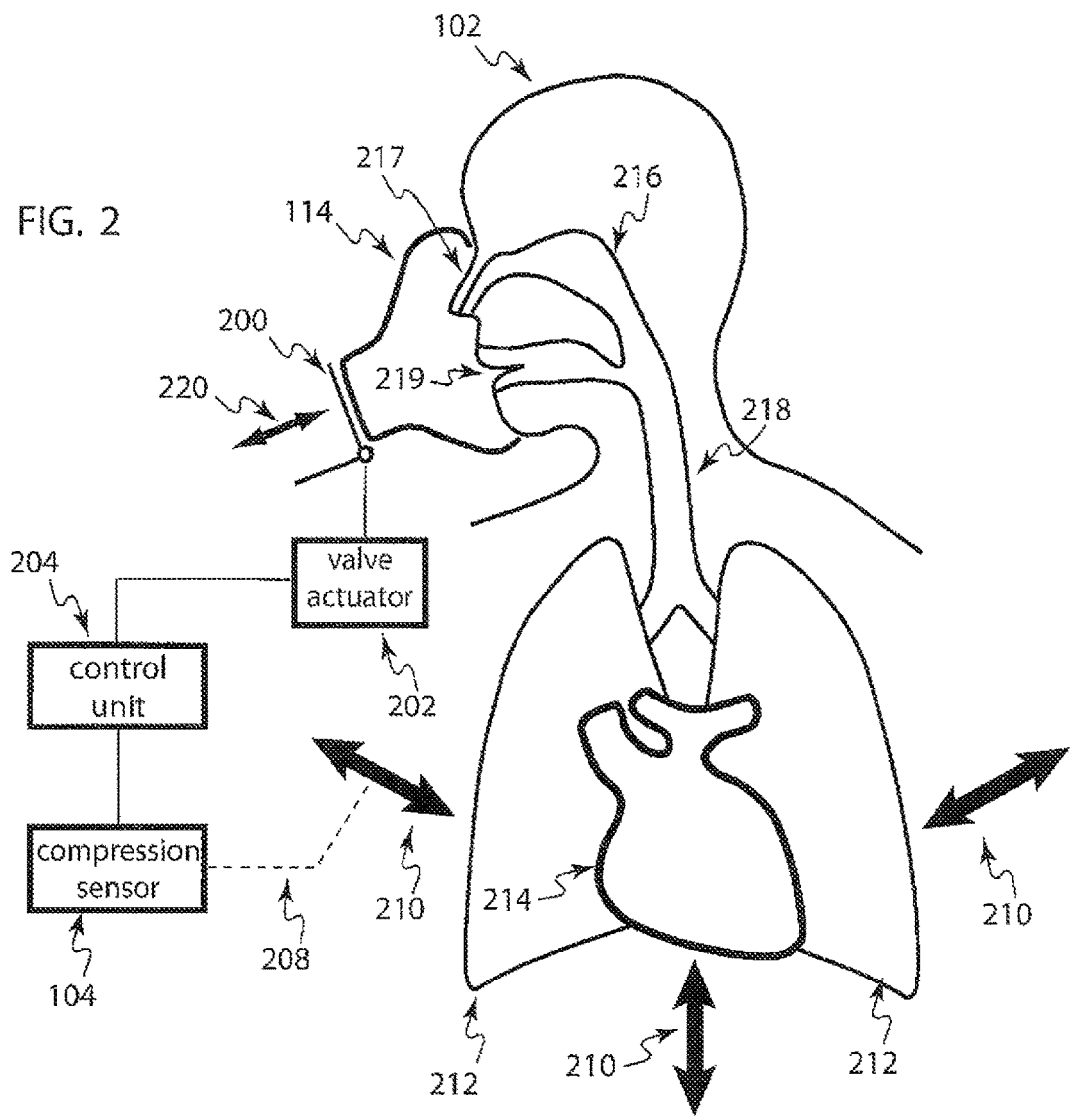
FIG. 2 shows the elements of this invention, when embodied with a facemask.

FIG. 2 illustrates in block diagram form the invention embodied with a facial mask 114 coupled to patient 102. Control of the upper airway 216 and lower airway 218 is established with the mask 114 covering nose 217 and mouth 219, and by ensuring an air seal against the facial skin of the patient 102. Such air seals and mask construction is conventionally known in the field of anesthesia, emergency medicine, and the like. However, the present invention includes a valve 200, that is inventively controlled, either to close or open the flow of air 220 to and from the patient's respiratory system. Valve 200 is operated to open or close via valve actuator 202. Valve 200 may be embodied in various forms for the purposes of this invention, for example, by a flap occluding a tube passage way, a needle plunger against a hole opening, or any other pneumatic valve method known to those skilled in the art of air flow control for medical devices. Actuator 202 may be a solenoid, a servo, a pneumatic piston system, or any other conventional pneumatic valve activation system. These constitute means to actuate the valve 200. Control unit 204 provides the signal or energy to actuator 202, so that valve 200 opens and closes at the appropriate times, inventively synchronized and sequenced according to the invention, as will be further described below. Compression sensor 104 senses when forces 210 are applied to the thorax of the patient during the CPR procedure. Dashed line 208 shows this sensing relationship. The information from sensor 104 is coupled to control unit 204, so it can achieve the inventive synchronization and sequence of control of valve 200, as will be later described herein.

Control unit 204 may be implemented in various ways known to those skilled in the art of electrical control. In one embodiment of this invention, a microprocessor or microcontroller may be used. The microcontroller or microprocessor may include at least one timer and at least one memory storage location to save timing information. The microcontroller may also include an arithmetic unit to provide basic mathematic computations, and basic signal processing techniques, as is generally known in the art of microprocessor based medical devices. Alternatively, a simpler non-program based sequential circuit can be used, using sequential electronic circuits could be used. In another implementation, an analog electronic circuit could be constructed to provide the required control signals to valve 202.

The functional blocks shown in FIG. 2 can be variously located, achieving in all cases the objectives of the invention. For example, the compression sensor 104 may physically include the control unit 204. In a flattened bellows embodiment of the sensor 104, the control unit can be included as a circuit inside the bellows. Alternatively, control unit 204 may be instead included as part of mask 114. For instance, control unit 204, valve actuator 202, and valve 200 may all be included in one assembly, the airflow control assembly 110 illustrated in FIG. 1. Other physical dispositions of the functional blocks 104, 204, 202, and 200 may be used, without departing from the spirit of the invention.

FIG. 2 also shows the lungs 212 of the patient 102, shown here in an undefined and general inflation state. As will become apparent further below, the amount of air inflation of lungs 212 is an important factor in the operation of the invention. Heart 214 is also shown in a general undefined state of ventricular blood filling. As will also become apparent later in this description, the amount of ventricular blood filling of heart 214 is another important factor in the operation of the invention. Thoracic compression and decompression forces 210 typical of CPR are shown as they relate to the lungs 212 and heart 214.

Figure 3:
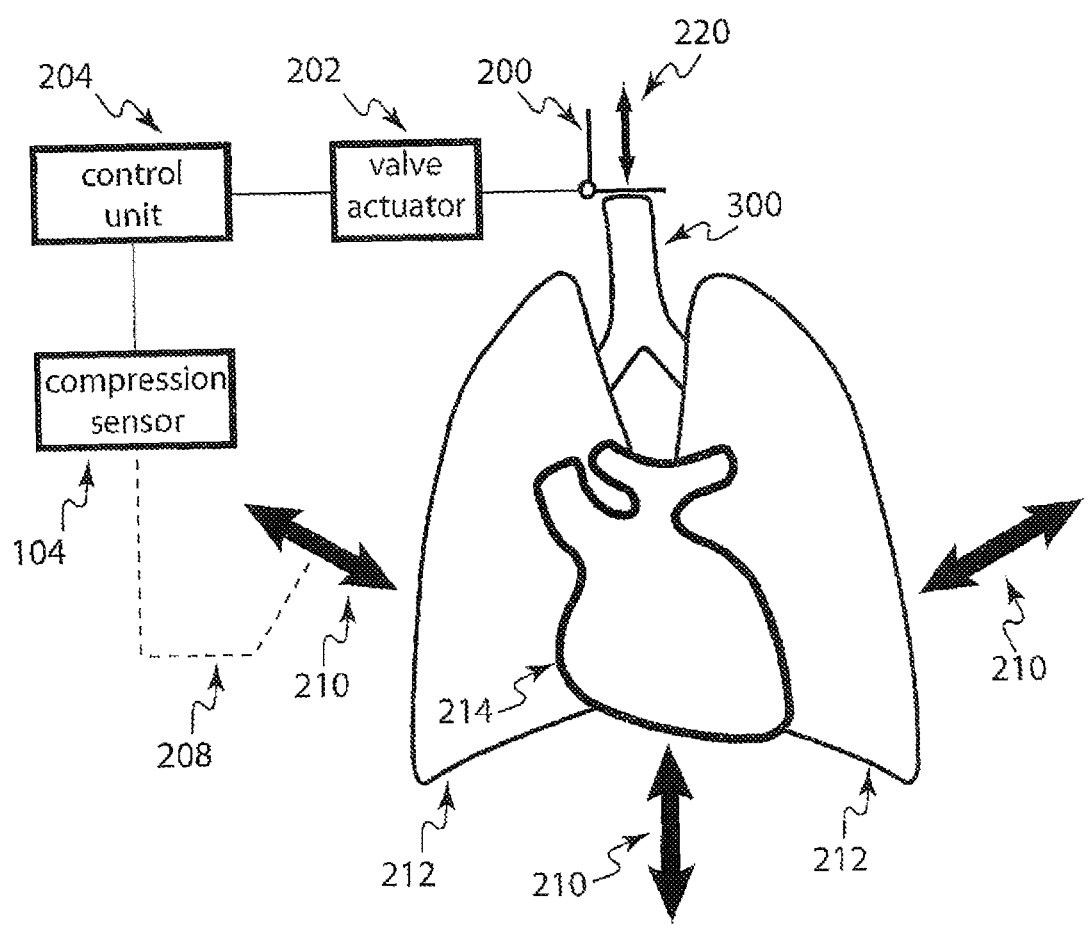
FIG. 3 shows in a more general manner the elements of this invention, when embodied with a valve located anywhere along the patient's airway.

Similar to FIG. 2, the diagram in FIG. 3 more broadly describes the invention by showing that it can be embodied with an airway valve 200 located anywhere as long as the flow of air 220 from the lungs 212 of the patient is controlled. The airway 300 of the patient 102 is shown here as the trachea. As such a tracheal tube could include valve 200, provided a good air seal is achieved so that exclusive control of airflow is made by valve 200. Other locations of the valve 200 can be used and still be within the limits of the invention. For example, the valve could be on a mouthpiece, as part of an upper airway device, or other airway devices know to those skilled in the art of medical artificial ventilation. Besides this generalization of airway control, all labels and functional blocks are as noted for FIG. 2. Thus, said tracheal tubes and upper airway devices constitute known sealing means to control the airway of the patient.

FIGS. 4A-4E and FIG. 5. show the five state sequence of cardio pulmonary states achieved with this invention. The states are labeled with numerals 401 to 405, and are shown in FIGS. 4A-4E, respectively. These five states are also shown at the top of the timing diagram of FIG. 5, and correspond to the events shown in the traces below them. Throughout this document it is clear that these states follow that sequence in order, from 401-405 in sequential order, and then recommence again with 401, then 402, 403 and so on continuously, for the duration of the CPR procedure. The inventive device enables that advantageous sequence, with each state having a particular cardio pulmonary and valve condition.

In the following detailed description, FIGS. 4A-4E and FIG. 5 will both be referenced to explain the operation of the inventive device, and its advantages. Beginning with the description of state 401 in FIG. 4A, the invention provides for a closed airway valve 200 during the application of CPR thoracic compression 411. In this state 401, the lungs 212 are inflated to the maximal inflation amount, as previously achieved in the preceding decompression of the chest with an open airway, namely state 405. In this description of the inventive cardiopulmonary sequence, the term "maximal inflation" is in the context of CPR, and therefore does not refer to the maximal inflation achieved for example by a large voluntary inhalation, that is, a conscious vital capacity inflation, as is known in conventional respiratory physiology. In the case of passive decompression CPR, where after a compression the chest naturally re-expands due to the elastic recoil of the rib cage and thorax, the maximal inflation refers to the amount of air present in the lung at the end of such recoil with an open airway. As can be easily discerned, such inflation will be greater if the airway is widely open. In the prior art, airflow restriction devices may prevent full inflation of the chest. In contrast, in this invention, the state 401 has more air because it was preceded by a decompressed state 405 with an unrestricted airway.

In some embodiments, even more air could be present if active lung inflation structures are provided to act during state 405, for example with a bag, or a mechanical ventilation device, as is known in the art of artificial ventilation for patients.

With that distinction from prior art, FIG. 4A shows state 401 where the lungs 212 are maximally inflated and the airway is occluded completely by closed valve 200. A CPR compression 411 is delivered. Because the airway is occluded in this state 401, and the lungs 212 are maximally inflated, the compression force is best transmitted to the heart's ventricles and a maximal ejection is achieved. Again, here "maximal" refers to the context of all possible ejections that can be achieved during CPR. As will become apparent, the reason for this maximal ejection is that the heart was filled by a maximal intrathoracic vacuum in preceding state 404. Further, the greater lung inflation of lungs 212 provide better lateral mechanical support in squeezing the heart. If the lung inflation was less, the heart would more easily expand into the lateral spaces when the chest is compressed in the antero-posterior direction. Such is one advantage of this invention: a compression with maximally inflated lungs providing better lateral support to the heart. Heart 214 is thus drawn in state 401 as maximally squeezed, as compared to the other states.

Figure 5:
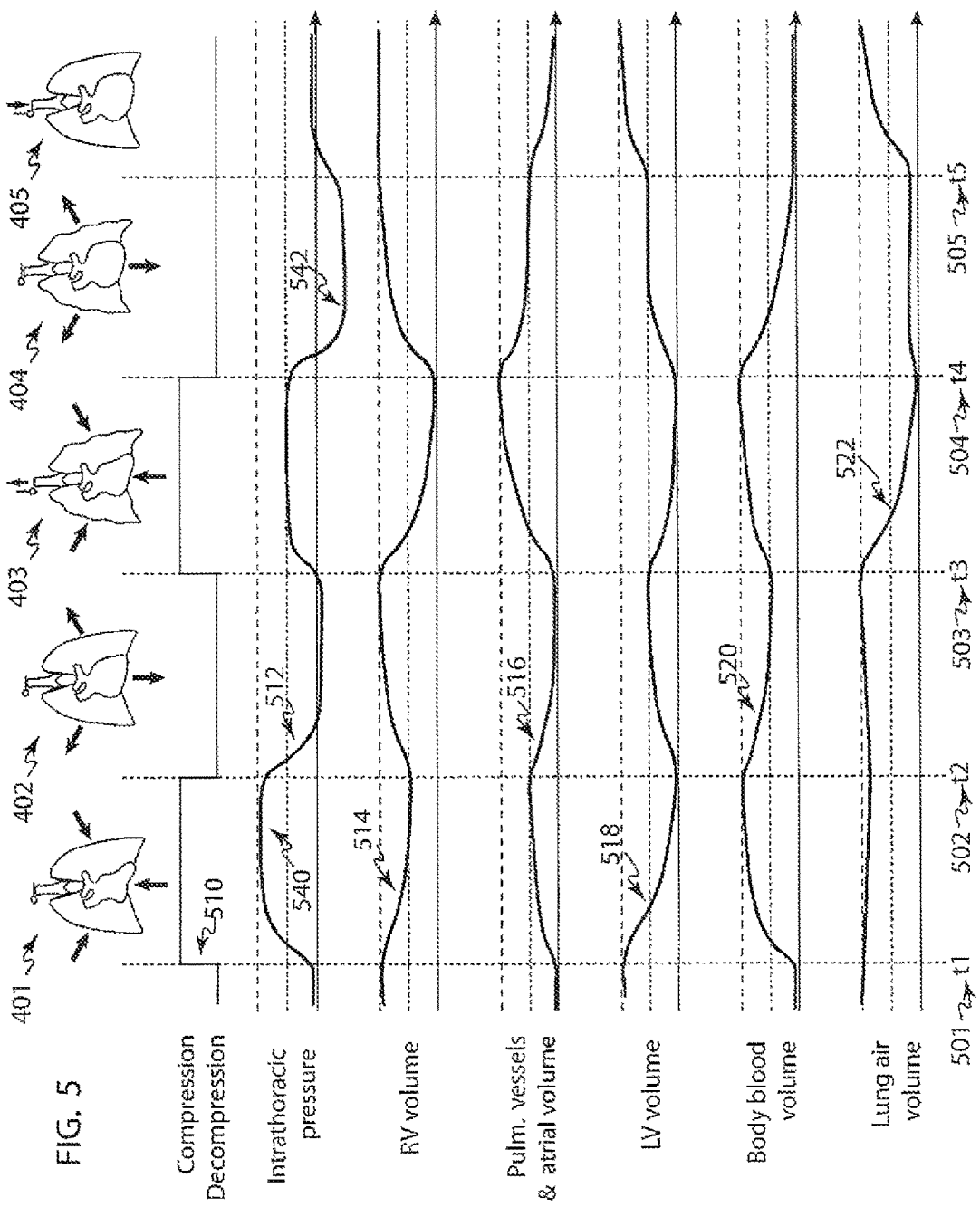
FIG. 5 shows in greater detail a sequence of intrathoracic pressures, cardio-pulmonary cycles, and airway valve states in accordance with one or more examples of the present invention.

Now referring to FIG. 5, the intrathoracic pressure and cardio pulmonary volumes are shown during each state. Trace 510 shows the timing of application of chest compressions and decompressions during the CPR procedure. The passage of time proceeds to the right in a conventional manner. The instants of time when the states change are marked t1 through t5 at the bottom of the figure, and labeled with numerals 501 through 505 respectively. Circulating blood volumes in the various compartments of the circulatory system are shown in traces 514, 516, 518, 520. These volumes represent only the differential circulating blood volume, not the total blood volume of the compartments. It can be appreciated that as the pumping of blood occurs, blood moves from one compartment to the other, with some elastic storage occurring in the various components. For instance, in a normal conscious individual, a differential blood volume in circulation can be 70 milliliters (ml), a typical ventricular volume ejected by the heart, and stored in part in the arterial compliances. In contrast, the total absolute blood volume in the body can be about 5 liters. This clarifies the concept of differential versus absolute blood volumes of the circulation that are used in this document.

In all of the following discussions reference is only made to this differential concept of blood volumes in the circulation. Accordingly, in FIG. 5, and as an exemplary description in a typical adult patient, each vertical axis division marked by horizontal dashed lines represents about 50 ml of blood. Illustrating the use of the vertical scales, in state 401, the body blood volume 520 gains 100 ml as a result of a chest compression causing a maximal left ventricular ejection between the times t1 501 and t2 502, whereas the right ventricle ejects 50 ml, as seen in trace 514 during the same period of time.

The sum of the differential circulating volume of blood remains constant when added across all compartments, as no new blood is being created, of course. If one adds the end volumes of all traces 514, 516, 518 and 520 at any instant of time t1, t2, t3, t4, t5 (labelled 501 to 505), one obtains a constant volume of 400 ml, in this example.

It is noted that these scales and volume quantities are illustrative only, and serve in the following description to explain the operation of the invention. Different quantities may appear in practice with the varying size of individuals, so that the use of specific quantities below should not be construed as a limitation of the invention.

Traces 514, 516, and 518 refer to the cardio pulmonary circulating blood volumes, as labeled in FIG. 5. Trace 520 refers to the balance of the circulating blood, in the rest of the body, and excluding the heart and lungs. Trace 522 is an air volume trace denoting volume of in the lungs 212.

Returning to the cardiopulmonary advantage discussion, and looking in FIG. 5 at state 401 in, and below it, the intrathoracic pressure 512 and all the volumes 514-520, one can appreciate that the intrathoracic pressure 512 is maximal during state 401, at about time 540. There is maximal left ventricular (LV) ejection as noted in trace 518, when the left ventricle ejects 100 ml maximally aided by a chest compression enhanced by inflated lungs and a closed airway. The right ventricle (RV) also ejects, but not nearly as effectively, because it must eject into a more resistive load: the relatively and positively pressurized lung. As such, trace 514 shows a moderate RV ejection of 50 ml during this state 401. Such ejection is mostly received by the pulmonary vessels, (pulmonary arteries and veins), as well as the left atrium, as noted in trace 516.

Continuing to the second state 402 in FIG. 4B, the chest is decompressed during the decompression phase of CPR. In this state the invention's control unit 204 and airway valve 200 provide for a closed airway. Because no air has been expelled from the thorax in states 401 or 402, the chest recoil of decompression state 402 will provide a moderate, not maximal, amount of intrathoracic vacuum. Since the lung is more full of air, some of the vacuum created by the passive recoil is absorbed by expansion of the greater air volume in the lungs. Therefore, this decompression does not offer as much intrathoracic vacuum as would be afforded if the lungs had less air to expand in the vacuum. That is why the vacuum is qualified as moderate in this description of state 402, and the heart 214 is illustrated in FIG. 5 with moderate filling: 50 ml enter each of the RV and LV as noted in traces 514 and 518, respectively. These volumes drain from the lung, atria, and body as evident in traces 516, 518, and 520.

Continuing now to the third state 403 in FIG. 4C, a chest compression delivered by a rescuer 100 applies compression 411 to the thorax, while the inventive device opens the airway valve 200 at instant t3 503 on trace 510. This happens when the sensor 104 and control unit 204 detect the beginning of a second compression in the five state CPR cycle, and therefore actuate the airway valve 200 via actuator 204 to an open position. In this state 403, a maximal RV ejection of 100 ml occurs as it ejects into a low air volume and open air way coupled lung. That is, the RV ejects its relatively high volume into a lower resistance load. The received high volume primes the pulmonary circulation and atria with a maximal differential blood volume of 100 ml, as noted in trace 516, at instant t4 504. Further, the compression 411 and open airway evacuate air 420 from the lungs to provide ventilation to the patient. This differential air evacuation can be seen in FIG. 5 trace 522. As will be apparent in the next state 404, this near maximal evacuation of the lung air will improve circulation by maximizing the vacuum 542 in the lungs 212.

Continuing now to the fourth state 404 in FIG. 4D, the sequence continues when the inventive device detects via sensor 104 the end of compression and the beginning of decompression at instant t4 504. At that instant, the airway valve 200 is closed, and the chest, relatively devoid of air from the prior state 403, recoils and passively expands to create a vacuum in the thorax. This is noted in FIG. 5 trace of intrathoracic pressure 512, where a maximal negative pressure, i.e. a vacuum, is achieved at 542. This vacuum, provided via a completely closed airway valve 200, provides the maximum vacuum that can be achieved via passive chest recoil. This is in contrast to prior art, where there is a partial restriction to the ingress of air, such that some vacuum is created, but not as great as when a complete occlusion of the airway is applied with a more empty lung. The greater vacuum further enhances the circulation by drawing more blood into the heart 214 from the lungs 212 and body. Such volume transfers during this high vacuum state 404 are noted in FIG. 5, in traces 514, 516, 518, and 520. The thoracic vacuum contributes to pull 100 ml from the body into the right side of the heart mostly, as seen in body volume trace 520 losing 100 ml, and the RV gaining 100 ml, as evident in trace 514. The pulmonary vessels and right atria, (trace 516), subject to vacuum, and thus have more difficulty surrendering volume into the left ventricle, which only gains 50 ml (trace 518) during this vacuum state.

Continuing with the final state of the cycle, state 405 in FIG. 4E and FIG. 5, the inventive device opens the airway valve at instant t5 505 in FIG. 5. This is a "pause" state in the CPR cycle proposed with this invention. It allows for intake air 422, facilitated by the intrathoracic vacuum created in the previous state 404, and a completely open airway. The inflow of air is noted in trace 522 of FIG. 5, after time t5 505. The entering pulmonary air, and the elastic compliance of the pulmonary arteries recoiling from a lung vacuum, contribute to push blood forward towards the left side of the heart. In this example, about 50 ml of volume are added to the LV in this state 405. This is evident in lung vessels and atria trace 516 of FIG. 5 losing 50 ml for the benefit of the LV, trace 518.

The enhanced air inflow of this state 405 is in contrast to some prior art devices that enhance circulation with vacuum, but do not include a regular and periodic passive ventilation cycle with unrestricted airways as part of the CPR device. Whereas the prior art restrictive devices require interrupting the CPR or the vacuum creation to deliver occasional ventilations, the present invention has the advantage of including ventilation as part of the CPR cycling routine, without imposing significant pausing or interruption of either compressions or vacuum creation. The disadvantage of interruptions for ventilation delivery has been noted by, for example the March 2008 American Heart Association Science Advisory on CPR (Circulation journal citation: 2008; 117:2162-2167). As such, the current invention provides for advantageous periodic, uniform and continuous CPR cycles, with maximal vacuum and compression phases, as well as ventilation, all included in a five state cycle. The present CPR device invention could be used with an easily memorized verbal cue to be used by the rescuers: "pump-pump-pause". This is similar in concept to verbal cues used in dance classes, where the students are trained to use a "quick-quick-slow" step rhythm in following certain music. The "pump-pump-pause" cue could be delivered so that an approximate compression rate of 80-120 compressions per minute is delivered, in accordance to widely accepted optimal rates for CPR. Timing lights or tones could easily be incorporated to the invention, so as to aid the rescuer in the timing and cadence of the five states of the present invention, as is evident to those skilled in the electronic arts.

Returning to FIG. 5. it can be appreciated that the airway valve 200 opens at time t5 505, even though there is no leading or trailing edge of the compression sensor trace 510 at that time that could be used to trigger the airway valve 200 opening. In one embodiment of the invention, the moment of valve 200 opening at t5 can be determined by control unit 204 by keeping a timer that measures the rescuer's compression frequency and provides a delayed trigger from a feature of trace 510. In one embodiment, the control unit 204 could measure and store the time from leading edges in trace 510 at times t1 501 and t3 503, thereby establishing a time period T between compressions. The control unit could then introduce a delay of half the measured period, T/2, beginning at time t4 504, the second falling edge of trace 510. After said delay, at approximately t5 505, the control unit 204 causes the airway valve 200 to open. An advantage of this embodiment is that no assumption is made about the individual rescuer compression frequency: the compression period is automatically measured, and the timing of valve 200 opening at the start of state 405 is done accordingly. Other similar timing algorithms are possible based on various features of the sensor trace 510, which is accessible to the control unit, without departing from the scope of the invention. For example, to open the valve 200 in state 405, the control unit 204 could wait for a delay of one measured period T, beginning at time t3 503. Other similar trigger and delay techniques could be used to open the valve 200 at time t5 505. Similar techniques could be used to effect the valve closure at the end of state 405, corresponding to a new t1 time of a next cycle.

Figure 6:
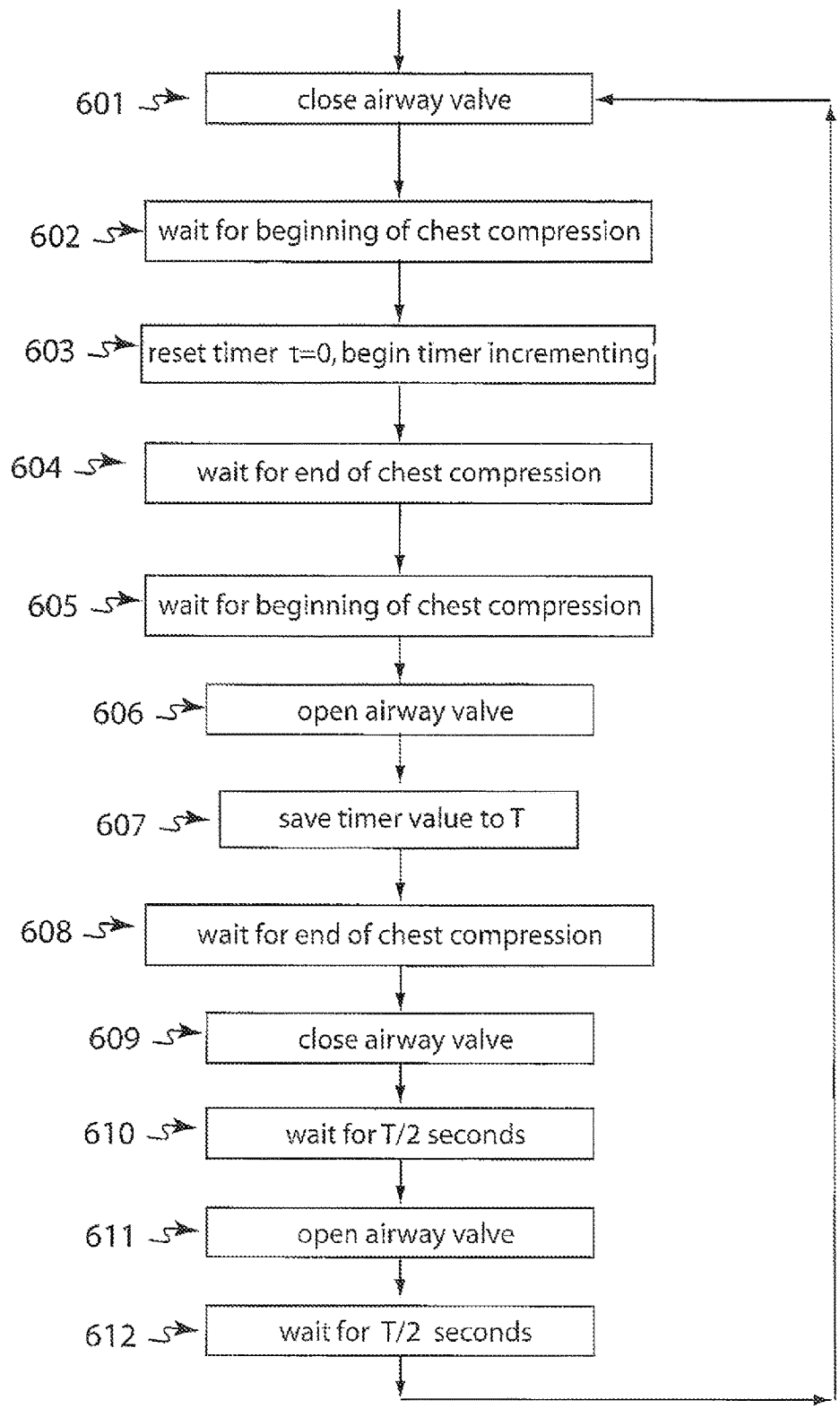
FIG. 6 shows a flow chart illustrating a control sequence used in an embodiment of the invention.

FIG. 6 shows a flow chart representing a control sequence of a microcontroller or microprocessor included in a control unit 204 (FIG. 3) of one embodiment of the invention. The control sequence shown in FIG. 6 realizes the cardio pulmonary state sequence shown in FIGS. 4A-4E and FIG. 5 by properly activating valve 200 in synchrony with the information of compressions and decompressions obtained from sensor 104 (FIG. 3). The control sequence begins at state 401 shown in FIG. 4A, by having the control sequence at step 601 with a closed airway valve. Next, the microcontroller enters a wait loop at step 602, waiting for the signal 510 (FIG. 5) from the compression sensor 104 (FIG. 3) to have a rising edge, as in time t1 501 in FIG. Such edge may be detected by the microcontroller reading an input pin, for example. Or alternatively, by having an intervening Schmitt trigger circuit as interfaces into the microcontroller sensor input, as is known in the electronic arts. Once the beginning of the first compression is detected, control passes to 603, a step in which a timer is set to zero. The timer is preferably inherent to the microcontroller in control unit 204, but may also be external to it. At this step 603, the timer is also set to begin counting the passage of time, that is, incrementing. In the next step 604, the control sequence enters a wait loop to wait for the compression to end, marking the end of state 401 at time t2 502 (FIG. 5). In the next step 605, the control sequence waits in state 402, until a compression is detected. This occurs at time t3 503 (FIG. 5), and then in the following step 606 the microcontroller provides a signal or energy to open airway valve 200, thereby implementing state 403 (FIG. 5). Also, at that instant of time t3 503, the timer value T is stored by the microcontroller in step 607. In essence the timer value T constitutes a measured period of compression frequency being delivered by rescuer 100. By using this information, proper activation of the airway valve 200 will be achieved in a manner related to the individual compression frequency. This valve activation occurs later at time t5 505, when there is no compression change, as seen in trace 510 at t5 505. After step 607, control then passes to step 608, where the end of the compression is awaited. This occurs at time t4 504, marking the end of state 403 (FIG. 5), and control passes then to step 609, in which the airway valve 200 is closed. State 404 (FIG. 5) is then begun. Proceeding to the next control step 610, said state 404 is held for a period of time T/2 (half of T), until time t5 505 (FIG. 5). Control then passes to step 611 in which the airway valve is opened, marking the beginning of state 405 (FIG. 5). Control then passes to step 612, in which a second delay of T/2 is used, establishing the duration of state 405 (FIG. 5). Incidentally, the sound of the air way valve 200 closing and opening, or only closing, can be used by the rescuer 100 to know when to begin the next compression. Alternatively, beepers, buzzers, light signals can be provided in an embodiment to indicate the beginning of the new cycle with state 401, and cueing rescuer 100 to deliver a compression. After completing step 612, control return to the original step 601, and the valve is closed in expectation of the next compression from the rescuer 100. In this way control continues as before, and the entire control sequence of FIG. 6 is repeated.

Figure 7:
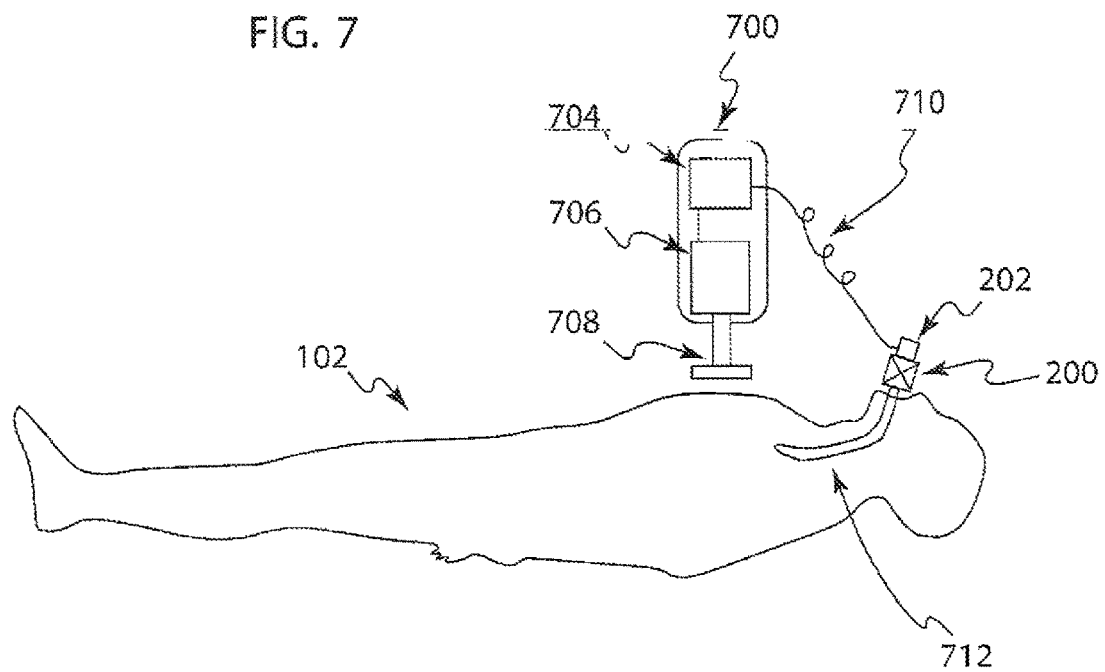
FIG. 7 shows an embodiment of the invention wherein a chest compression unit is used to deliver compressions to the patient and control the airway valve.

FIG. 7 shows an embodiment of the invention that includes a compression unit providing CPR to a patient 102. The unit provides active compressions and optionally, active decompressions, so that it functionally replaces the human rescuer. These units are well known in the art of cardiac resuscitation. One example is the "Lucas CPR" (trademark) unit, manufactured by Jolife AB of Lund, Sweden. A description of such devices is given in U.S. Pat. No. 7,226,427 to Steen. In essence, these mechanical chest compression units constitute means to deliver mechanical compressions to the chest of a patient, thereby relieving human rescuers from the fatigue of manually giving compressions. The unit also ensures that the timing and regularity of the compressions is kept appropriately. Relative to the present invention, FIG. 7 shows an embodiment where the airway valve previously described in this document is controlled in coordination with a compression unit, but still achieving the timing described in FIG. 5. In this embodiment of FIG. 7 however, the timing control of the valve can be achieved without the previously described compression sensor 104. This is because the control unit 704 commands the compressions, and therefore knows when the compressions are being delivered and not delivered. In this way no chest sensor is needed to know when compressions and decompressions are present, and the inventive control of the airway in synchronization with the compressions as shown in FIG. 5 can be achieved. In detail, FIG. 7 shows a CPR compression unit 700, containing a control unit 704, coupled to an actuator mechanism 706 that activates a piston plunger 708 or similar device that contacts the patient's chest, in manners known in the art of automatic CPR machines. Control unit 704 is also coupled via electric conductor 710 to airway valve actuator 202, which effects the closing and opening of valve 200, as previously described, and accordance to the timing shown in FIG. 5. In this embodiment of FIG. 7, the present invention is shown with a tracheal tube 712 as the means to control the airway of the patient. Tracheal tube 712 may include a sealing collar, or be sized to achieve a substantial airtight seal, enabling the positive and negative airway pressures of this invention, as already described. Such tracheal tube, its sealing collars and similar devices have long been known in the art. These constitute sealing means to control the airway of the patient and could have been used as well as those as those sealing means to control the airway of the patient such as a facemask 114 mentioned previously, or any other airway control device known in the art of ventilatory support medicine.

Figure 8:
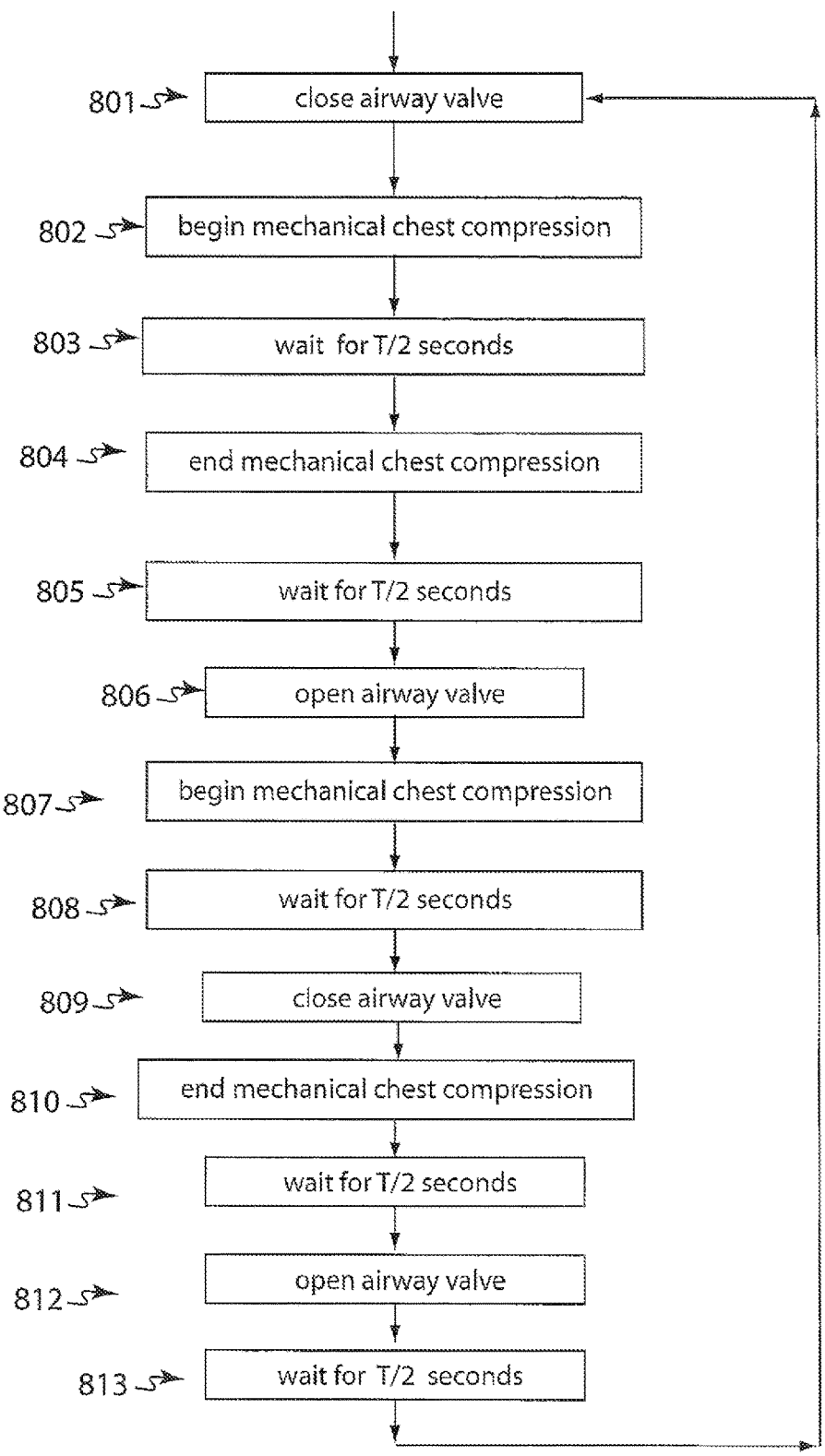
FIG. 8 shows a flow chart illustrating a control sequence used in an embodiment of the invention that includes a mechanical compression unit.

FIG. 8 shows a flow chart representing a control sequence of a microcontroller or microprocessor included in a control unit 704 of the embodiment described in FIG. 7. The control sequence shown in FIG. 8 realizes the cardio pulmonary state sequence shown in FIGS. 4A-4E and FIG. 5 by properly activating valve 200 in synchrony with the information of compressions and decompressions delivered by compression unit 700 (FIG. 7). The control sequence begins at state 401 shown in FIG. 4A, by having the control sequence at step 801 with a closed airway valve. Next, the control unit 704 commands the mechanical compressor system of actuator 706 and plunger 708 to deliver a compression in step 802. Once the beginning of the first compression is effected, control passes to 803, a step in which a timer waits for an interval of T/2 (half of T) seconds, where T is a programmed time interval between successive compressions. A typical range of values for T could be 0.3 to 0.75 seconds, in accordance to known optimal compression rates, as is known in the art of CPR. For instance, T could be programmed to 0.6 seconds. The programmed interval could be programmed once only at manufacture, or alternatively, be user programmable. The timer is preferably inherent to the microcontroller in control unit 704, but may also be external to it. In the next step 804, the control unit 704 effects the end of the mechanical compression, commanding actuator 706 to lift the plunger 708 off from the patient 102. This marks the end of state 401 at time t2 502 (FIG. 5). In the next step 805, the control sequence waits in state 402, for T/2 seconds. In step 806, the airway valve 200 is opened as before, and in step 807 a compression is initiated. This occurs at time t3 503 (FIG. 5). Control then passes to step 808, where a wait of T/2 seconds takes place. This occurs at time t4 504, marking the end of state 403 (FIG. 5), and control passes then to step 809, in which the airway valve 200 is closed, and in step 810, the compression is terminated. State 404 (FIG. 5) is then begun. Proceeding to the next control step 811, said state 404 is held for a period of time T/2, until time t5 505 (FIG. 5). Control then passes to step 812 in which the airway valve is opened, marking the beginning of state 405 (FIG. 5). Control then passes to step 813, in which a second delay interval of T/2 seconds is used, establishing the duration of state 405 (FIG. 5). After completing step 813, control returns to the original step 801, and the valve is closed in preparation for the next compression from the compression unit 700. In this way control continues as before, and the entire control sequence of FIG. 8 is repeated. It is understood that variations in the duration of the intervals described can still be present without departing from the scope of the invention.

In yet a further embodiment, and referring again to FIG. 7, the compression unit 700 includes a compression sensor (not shown) coupled mechanically to plunger 708 and electrically to control unit 704, to provide the knowledge to the microprocessor of when the compressions are actually occurring. This would allow for delays in the actual contact to the chest of the patient from the moment that a compression or decompression command is given by the control unit 704. In this embodiment, the implementation of the required steps to achieve the timing and enhancements described in FIG. 5 would be an obvious combination of the steps in FIG. 6 and FIG. 8, as will be apparent to those skilled in the firmware engineering arts.

Figure 9:
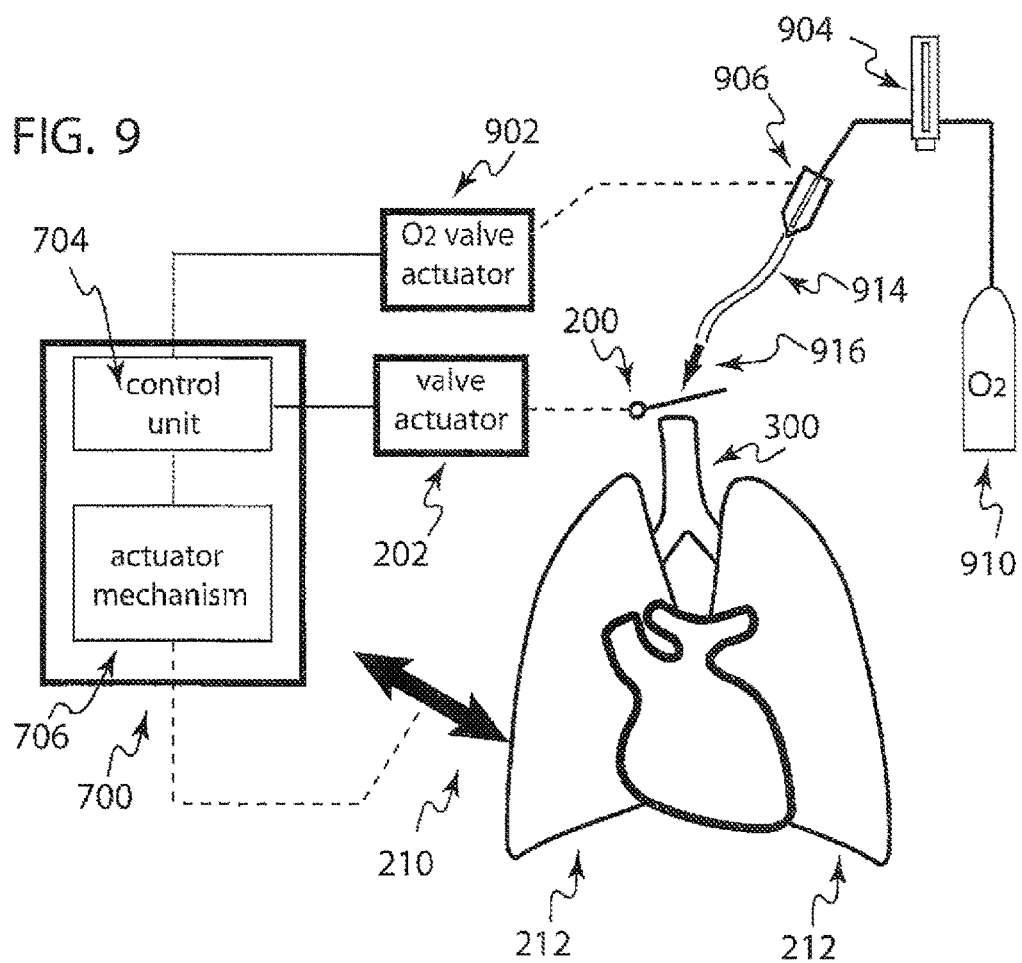
FIG. 9 shows an embodiment of the invention including a chest compression unit and with oxygen injection to provide ventilation to the patient.

In a further embodiment of the invention, shown in block diagram form in FIG. 9, the inventive system described in FIG. 7 can additionally include means to provide gases to the patient, such as oxygen. Referring to the embodiment of FIG. 9, a compression unit 700 as already described is shown. It delivers mechanical forces 210, automatically onto the chest of a patient with heart 214 and lungs 212. Compression unit 700 is constructed in a manner similar to that described for the embodiment of FIG. 7, above. Control unit 704 is implemented with a microprocessor, micro-controller, a gate array, or any such device commonly known to those skilled in the arts of firmware engineering. It can perform the inventive sequence of the invention, using programmed steps as will be further described in relation to FIG. 10. Returning to FIG. 9, Control unit 704 controls an actuator mechanism 706 that applies forces 210 to the chest of the patient. Actuator mechanism 706 can be a pneumatic cylinder and piston system, in which a case a source of compressed air would be provided in the compression unit 700. This form of mechanical compression is well known in the art of mechanical resuscitation, and an example of it is described in U.S. Pat. No. 7,226,427 to Steen. Other actuator mechanisms could include electro-mechanical mechanisms, such as a reciprocating plunger powered from an electric motor and gears, as is commonly known in the mechanical engineering field. An example of such mechanism are the reciprocating saws commonly available in hardware stores, under the name 'saws all'. In any case of mechanical actuator 706, it can be controlled electronically by control unit 704, by conventionally known means (valves, switches, relays, etc). Control unit 704 also provides control signals to airway valve actuator 202, so as to provide occlusion or opening of valve 200 and thereby manage gas flow in the airway 300 of the patient. Control unit 704 in compression unit 700 also provides control signals to oxygen valve actuator 902, which actuates oxygen valve 906. Valves 200 and 906, and their actuators 202 and 902 are components that are well known in the art of pneumatic control. A flow meter 904 provides control of the magnitude of oxygen flow that is allowed when valve 906 is open. Alternatively, this embodiment of the invention can be constructed without flowmeter 904, if valve 906 is a proportional control valve. This type of electro-mechanical valve is well known in the art of pneumatic valve control, and provide a pre-determined flow of gas in accordance to the magnitude of a voltage or current applied to its actuator 902. That controlling voltage or current would be provided by control unit 704 in this embodiment of the invention. An oxygen source 910 is connected to valve 906, via flow meter 904, or if using a proportional control valve as element 906, directly to it. Oxygen source 910 could be realized by a simple tank and pressure regulator, as employed in many oxygen therapies in medicine, or a connection port to connect to an outside oxygen source of a hospital or ambulance. Oxygen is routed to the airway of the patient via a flexible plastic or rubber line 914. Oxygen line 914 delivers the jet 916 of oxygen at the airway of the patient. This can be done in one embodiment by passive oxygen inspiration, by locating the jet 916 of oxygen at the front of airway valve 200. In this way, when the patient passively draws air into his or her chest, and valve 200 is open, oxygen jet 916 provides oxygen to the patient. This occurs in state 405 of FIG. 5, which shows a sequence of states (already described) that the embodiment of FIG. 9 realizes. As the chest recoils from a chest decompression in state 405, valve 906 in FIG. 9 is opened, allowing oxygen to flow into the airway of the patient, and inflating the lungs in preparation for state 401 of the sequence (FIG. 5). It must be noted that in this description of ventilation, 'passive' refers to the fact that oxygen is not actively forced into the patient, as occurs with positive pressure ventilation known in the art of emergency medical care (for instance, with the well known bag-mask valve or BMV system). Returning to the description of how to construct the passive inspiration in the embodiment depicted in FIG. 9, it can be accomplished by simply disposing jet 916 immediately in front of the occluding element of valve 200. It is understood by those skilled in the arts of valves, that they typically have such an occluding element, such as a diaphragm, butterfly, ball with orifice, etc. Line 914 and jet 916 can be disposed in an airway management tube, such an endotracheal tube, or in a face-mask providing a substantial airtight seal, in any case so as to direct the jet of oxygen so it points into the airway 300 of the patient and thus improve its delivery and mixing with intratracheal and intrabronchial gases, and thereby minimize dead volume in ventilation.

An embodiment of the invention with active oxygen delivery can also be built, still maintaining the principles of enhanced circulation with the inventive sequence of the invention, explained in FIG. 5. To provide active delivery of oxygen, line 914 can be disposed into a face-mask or endotracheal tube that is applied to airway 300 of the patient, so that jet 916 is located distally to valve 200 (not in front of it, but beyond it and closer to the patient's lungs), so as to provide a pressurized oxygen delivery state 405 in FIG. 5. In this case, the inflow of oxygen would occur during that state 405 with airway valve 200 closed, so as to permit the pressurization of the airway with oxygen proceeding from source 910, via flow meter 904 (optionally), then via valve 906 and then through line 914. This would enable the full lungs required in state 401 of the invention, shown in FIG. 5. Exhalation of body gases including carbon dioxide would occur later in the inventive sequence, in state 403 of FIG. 5, with airway valve 200 of FIG. 9 open, oxygen valve 906 closed, all this during a compression effected by actuator mechanism 706. For embodiments of the invention with active oxygen delivery as described, injection of oxygen with valve 906 open occurs during state 405, and could further occur, during state 401 in FIG. 5, as both of these actions contribute to inflating the lung and providing a positive thoracic pressure that favors blood ejection in state 401 when a chest compression is being delivered. A one way valve to prevent backflow of oxygen during this state could be placed in series with valve 906, as is known in pneumatic circuit arts.

In the above descriptions of the embodiment of FIG. 9, it is understood that control unit 704 with a program or firmware in its memory, (as is commonly known in the art of microprocessors and microcontrollers), provides the control signals above described so as to realize the inventive sequence of cardio-pulmonary states of FIG. 5, which maximize the positive and negative pressures of the airway. When such pressures are applied synchronously with the compressions, an advantageous enhancement of circulation results, as described earlier in reference to FIG. 5.

The embodiment of FIG. 9 of the invention may also include a gasp sensor to resynchronize the inventive sequence of FIG. 5 to the gasp. Gasping occurs asynchronously relative to CPR compressions, often during emergency rescue of patients who have suffered long ventilatory or cardiac arrest, and consists of a breath taken by an unconscious patient occasionally, while otherwise not breathing. A sensor of gasping can be realized by a pressure transducer disposed in the endotracheal tube and unit 704 sensing a strong endotracheal vacuum, which occurs during a gasp. The gasping correction logic implemented in the firmware of unit 704 could detect the gasp, and if it does not occur in temporal coincidence with the vacuum states 402 or 403 of FIG. 5, the control sequence would be reset so that the sequence would proceed to be at state 405 when the gasp is detected, opening airway valve 200, and permitting oxygen or air ingress and fill the lungs. This state of full lungs after a gasp coincides with the full lungs description given earlier in reference to FIG. 5, and thus an advantageous synchronization is realized that maintains the enhanced circulation of the invention, while minimizing its disruption by gasps. Other mechanical gasp sensors, such as a band around the chest could also be used.

The scope of the embodiment described in FIG. 9 includes the delivery of other respiratory gases, or mixtures of them, such as oxygen and carbon dioxide to help maintain normal levels of carbon dioxide in the patient when the ventilations are relatively fast, for instance. Also included in the scope of the invention is the delivery of air, appropriate in emergency situations where oxygen sources are not readily available. In this case, elements 910 and 904 of the invention could be substituted by a flexible respirator bag and valve, similar to the one used in common bag-valve-mask (BMV) systems used in conventional emergency resuscitation. This would still be in the scope of the invention, as jet 916 could be air, and valve 906 would be connected to the bag system, which would provide pressurized air to the patient. In other words, the description given above for oxygen delivery elements can describe construction of this alternate embodiment with a respirator bag, substituting the oxygen source with the respirator bag, as will be obvious to those skilled in emergency ventilation.

Figure 10:
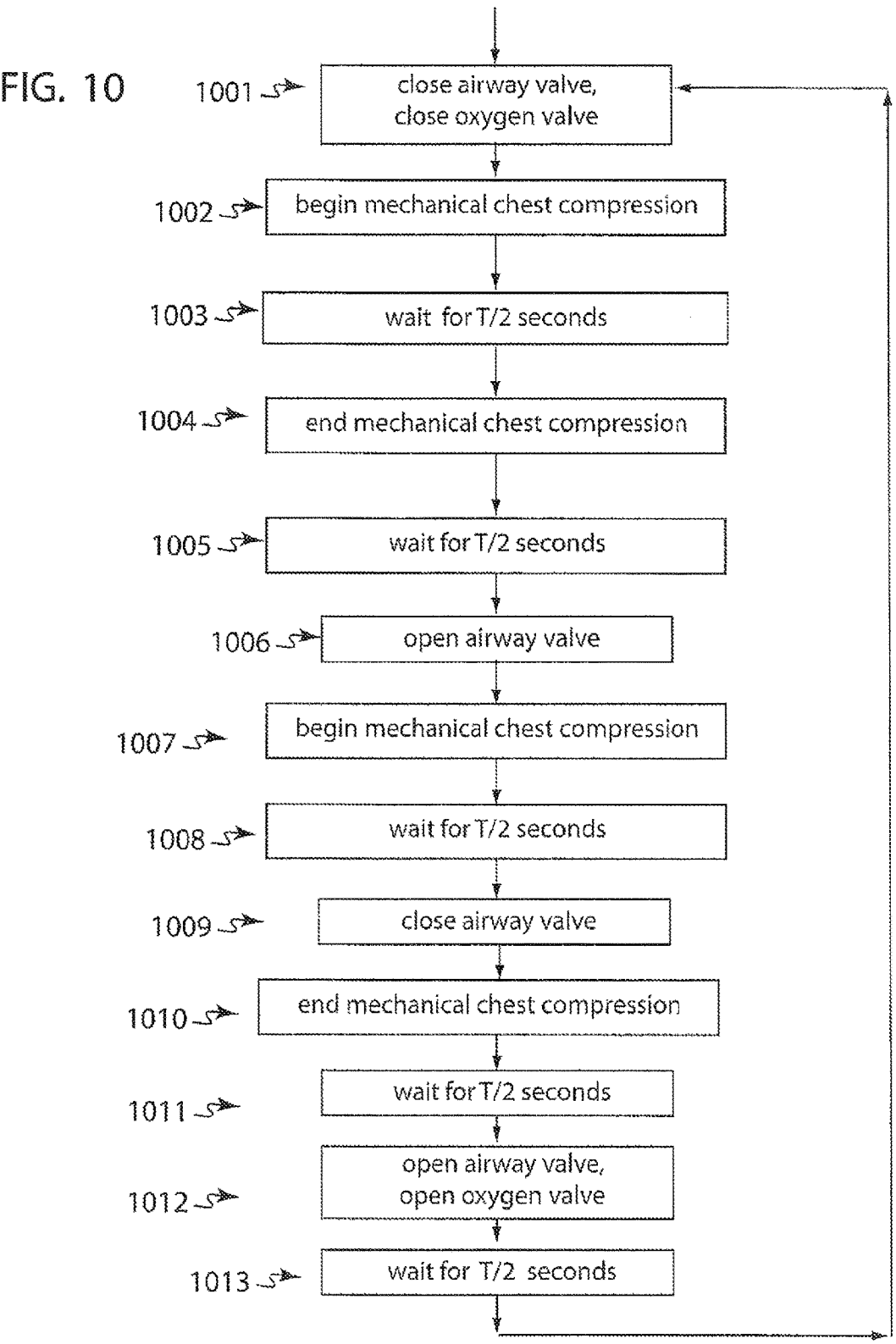
FIG. 10 shows a flow chart illustrating a control sequence used in an embodiment of the invention that includes a mechanical compression unit and oxygen delivery.

FIG. 10 shows a flow chart representing a control sequence of a microcontroller or microprocessor included in a control unit 704 of the embodiment described in FIG. 9. The control sequence shown in FIG. 10 realizes the cardio pulmonary state sequence shown in FIGS. 4A-4E and FIG. 5 by properly activating valve 200 in synchrony with the information of compressions and decompressions delivered by compression unit 700 (FIG. 9). The control sequence begins at state 401 shown in FIG. 4A, by having the control sequence at step 1001 with a closed airway valve 200 and a closed oxygen valve 906. Next, the control unit 704 commands the mechanical compressor system of actuator 706 to deliver a compression. Once the beginning of the first compression is effected, control passes to 1003, a step in which a timer waits for an interval of T/2 (half of T) seconds, where T is a programmed time interval between successive compressions. A typical range of values for T could be 0.3 to 0.75 seconds, in accordance to known optimal compression rates, as is known in the art of CPR. For instance, T could be programmed to 0.6 seconds. The programmed interval could be programmed once only at manufacture, or alternatively, be user programmable. The timer is preferably inherent to the microcontroller in control unit 704, but may also be external to it. In the next step 1004, the control unit 704 effects the end of the mechanical compression, commanding actuator 706 to lift the plunger 708 off from the patient 102. This marks the end of state 401 at time t2 502 (FIG. 5). In the next step 1005, the control sequence waits in state 402, for T/2 seconds. In step 1006, the airway valve 200 is opened as before, and in step 1007 a compression is initiated. This occurs at time t3 503 (FIG. 5). Control then passes to step 1008, where a wait of T/2 seconds takes place. This occurs at time t4 504, marking the end of state 403 (FIG. 5), and control passes then to step 1009, in which the airway valve 200 is closed, and in step 1010, the compression is terminated. State 404 (FIG. 5) is then begun. Proceeding to the next control step 1011, said state 404 is held for a period of time T/2, until time t5 505 (FIG. 5). Control then passes to step 1012 in which the airway valve is opened, the oxygen valve is opened, marking the beginning of state 405 (FIG. 5) and permitting the ingress of oxygen into the patient. Control then passes to step 1013, in which a second delay interval of T/2 seconds is used, establishing the duration of state 405 (FIG. 5). After completing step 1013, control returns to the original step 1001, and the airway valve 200 and oxygen valve 906 is closed in preparation for the next compression from the compression unit 700. In this way control continues as before, and the entire control sequence of FIG. 10 is repeated. It is understood that variations in the duration of the intervals described can still be present without departing from the scope of the invention.

In yet a further embodiment, and referring again to FIG. 9 and FIG. 7, the compression unit 700 includes a compression sensor (not shown) coupled mechanically to plunger 708 and electrically to control unit 704, to provide the knowledge to the microprocessor of when the compressions are actually occurring. This would allow for delays in the actual contact to the chest of the patient from the moment that a compression or decompression command is given by the control unit 704. In this embodiment, the implementation of the required steps to achieve the timing and enhancements described in FIG. 5 would be an obvious combination of the steps in FIG. 6 and FIG. 10, as will be apparent to those skilled in the firmware engineering arts.

Figure 11:
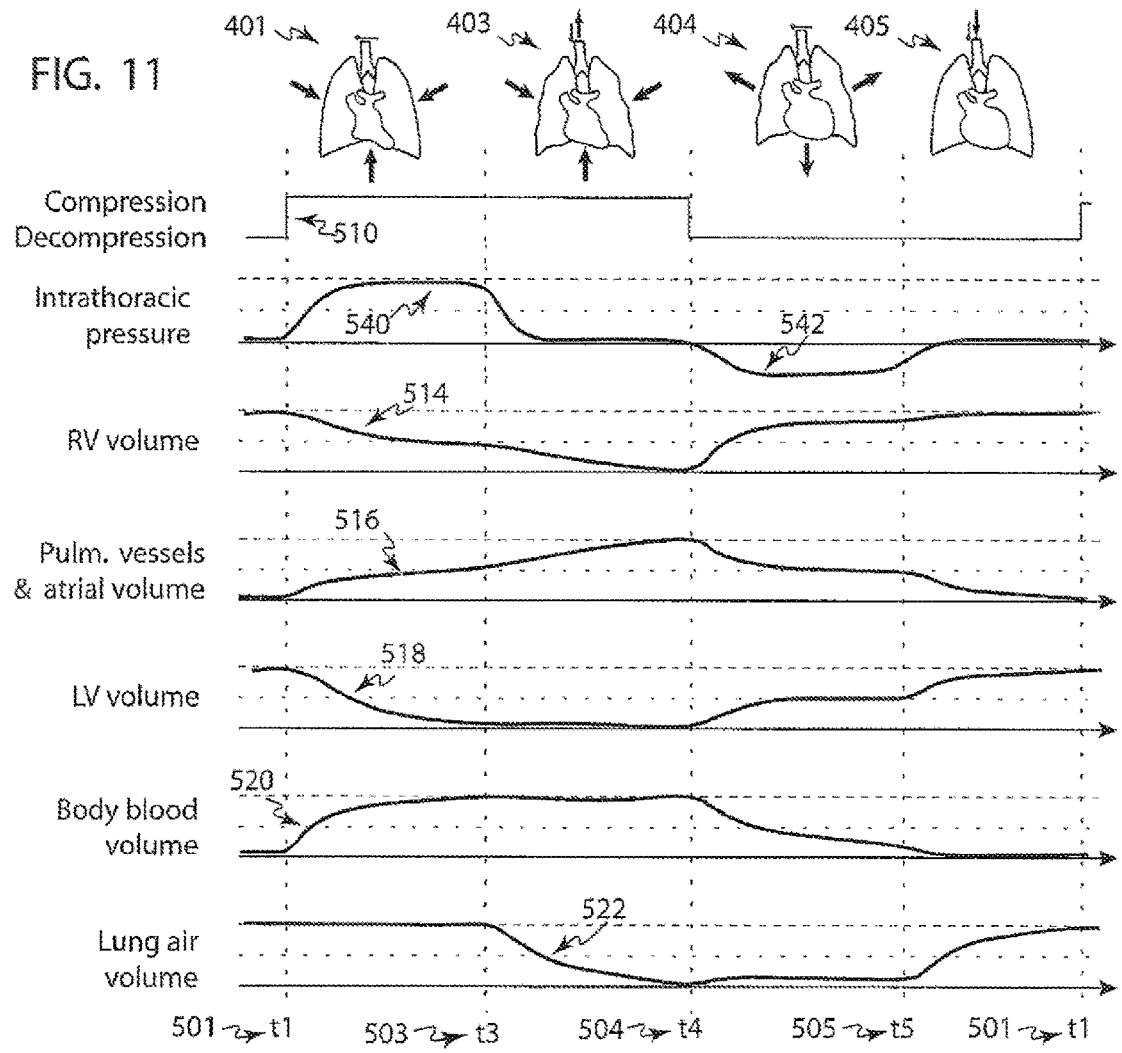
FIG. 11 shows a sequence of four cardio-pulmonary states and a regular cadence of chest compressions in accordance with one or more examples of the present invention.

In yet another embodiment, referring now to FIG. 11, it is possible to obtain the benefits and advantages of the invention using a four state CPR cycle. In essence, this embodiment is a simplification of the five state cycle shown in FIG. 5. The simplification is obtained by removing state 402. In this way, the four state CPR cycle shown in FIG. 11 is obtained, still including the advantageous positive pressure 540 to assist in thoracic ejection of blood during chest compression, and the negative pressure 542 to enhance vacuum and venous return of blood from the body blood volume. The labels in FIG. 11 are the same as for FIG. 5, and the specification, description and circulatory assistive mechanisms of the invention apply, as described before for the five state embodiment of FIG. 5. One difference in this four state cycle of FIG. 11 is that the airway valve is now opened during the compression (indicated by trace 510), for example at its midpoint, at time instant t3 503 in FIG. 11. In this way, the compression phase of the cycle has two distinct states 401 and 403. In the first, state 401, the chest is compressed with the lungs previously insufflated from the previous CPR cycle, and thus provides an optimized blood ejection from the thorax, just as was explained previously for state 401. In state 403 of FIG. 11 the airway valve is opened and the lung gases are vented out of the chest. This gas evacuation with an open airway sets up an optimal vacuum 542 when the airway valve is closed and the chest decompresses in state 404, just as was explained before for the embodiments using five states as in FIG. 5. As such, the rest of the CPR cycle in FIG. 11 continues as described before. One advantage of this four state embodiment of FIG. 11 is that the compression-decompression cadence is regular, and not in couplets as in FIG. 5. The advantage is given because it is the traditional form of CPR, as practiced for over 40 years, to use a constant, regular rhythm of compression decompression. To construct the embodiment that effects the timing cycle of FIG. 11, the apparatus described earlier in this document in reference to FIG. 1, FIG. 2, FIG. 3, FIG. 7, FIG. 9, can be used. That is, the inventive apparatus effecting the timing of FIG. 11 could be built as described earlier in this document in conjunction with a face mask, or with advanced airway such as an endotracheal tube, an oropharyngeal airway device, as described earlier. Similarly, the timing of FIG. 11 can be effected by an embodiment using a mechanical compression device (FIG. 7), and any of these (the mask, the advanced airway, or the mechanical compression system) could also include oxygen insufflation, as was previously described for the embodiment of FIG. 9.

Figure 12:
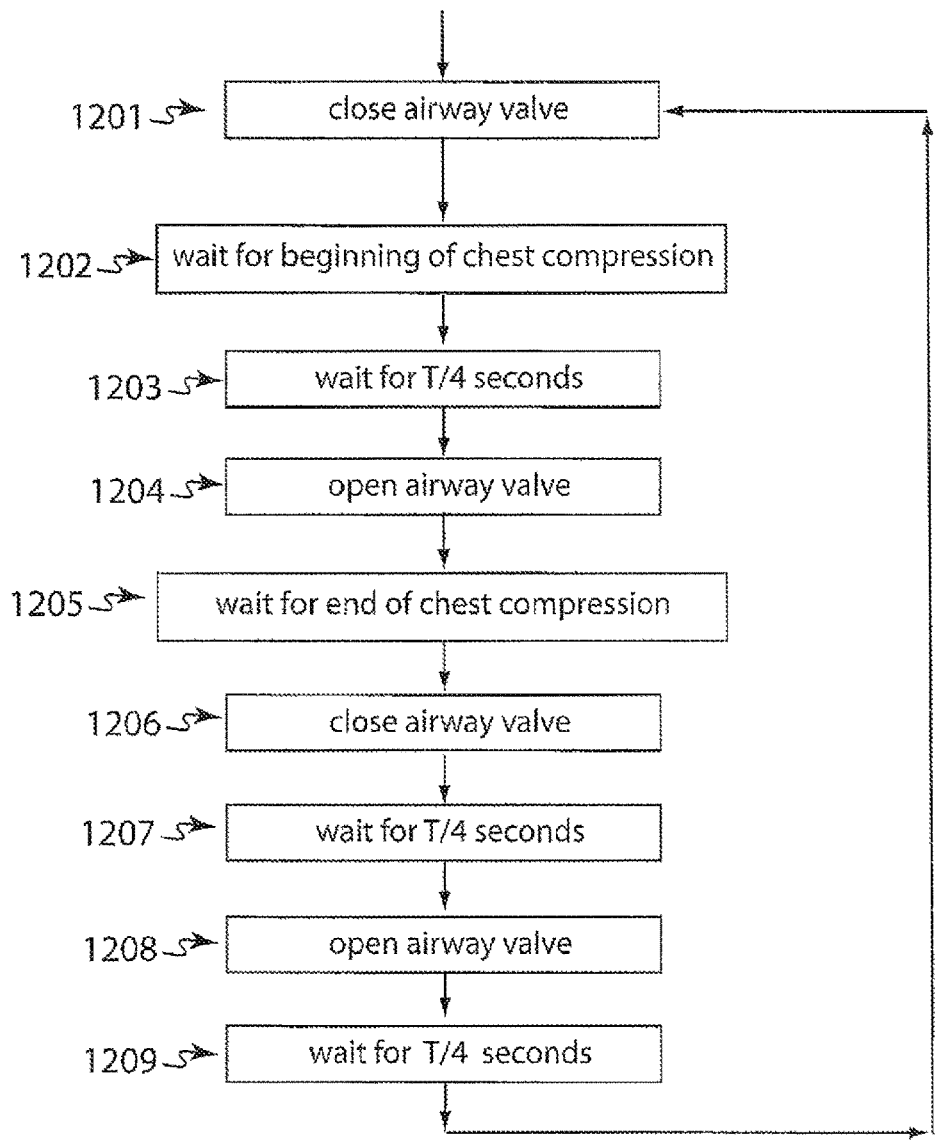
FIG. 12 shows a flow chart illustrating a control sequence used in the embodiment of the invention using a four state CPR cycle with regular cadence.

To provide greater detail on the manual compression embodiment given in FIG. 1 and FIG. 2, but using the four state timing of FIG. 11, FIG. 12 describes the algorithm that a control unit 204, as known in the art of electronic microcontrollers, could use to effect the timing of FIG. 11. In step 1201 of FIG. 12, the control unit 204 begins the CPR cycle by closing the airway valve 200 by means of valve actuator 202. The control unit 204 then obtains information (like a signal) from compression sensor 104, and in step 1202 waits until a compression cycle is initiated. Once the control unit 204 detects that event, control passes to step 1203, where a pause in control occurs. This corresponds to state 401 in FIG. 11. The pause is held for approximately T/4 seconds, where T is the period (in seconds) of the CPR cycle. That is, T is the total length of time in seconds for a compression and decompression to occur. The value T can be obtained by any time interval measurement methods, such as those well-known to those skilled in micro-controller instruments. In addition, methods developed in the future may be used without departing from the scope if this invention. For example, a few CPR cycles could be performed during which the control unit 204 would measure the average period T that a rescuer 100 is using. A few cycles could be averaged, for example, by 4 or 8 cycles, but any number could be used without departing from the spirit of this invention. Other estimations of period may be used, such as the median or the mode. During the beginning of the rescue effort, or after any interruption, the control unit 204 could command the valve actuator 202 to keep valve 200 open, until the period T has been measured as above. Then the synchronous opening and closing of the valve 200 could start, in accordance to the invention, so as to effect the timing cycles required by FIG. 11. Continuing with the description of the apparatus of FIG. 2 that uses the timing cycle of FIG. 11, we proceed in FIG. 12 to step 1204, after the T/4 seconds pause of step 1203 has elapsed. In step 1204, the valve 202 is opened via actuator 202, as commanded by control unit 204. It then waits for the end of the chest compression, in step 1205. This corresponds to state 403 in FIG. 11. The end of the compression moment t4 504 is determined when the control unit 204 receives such information from compression sensor 104 (FIG. 2). Control then proceeds to step 1206, where the valve is closed, so as to create the state 404 (FIG. 11). A pause of T/4 seconds occurs in the next step 1207 during this state 404. After that pause control proceeds to step 1208, at moment t5 505, and the airway valve 200 is opened to permit the entry of gases into the lungs. This occurs in step 1209, during a pause of T/4 seconds, effecting state 405, similar to what has been described earlier in this document. Control then returns to step 1201, and the CPR cycle begins anew. Other timing intervals can be used approximating T/4, without departing from the spirit of the invention.

Figure 13:
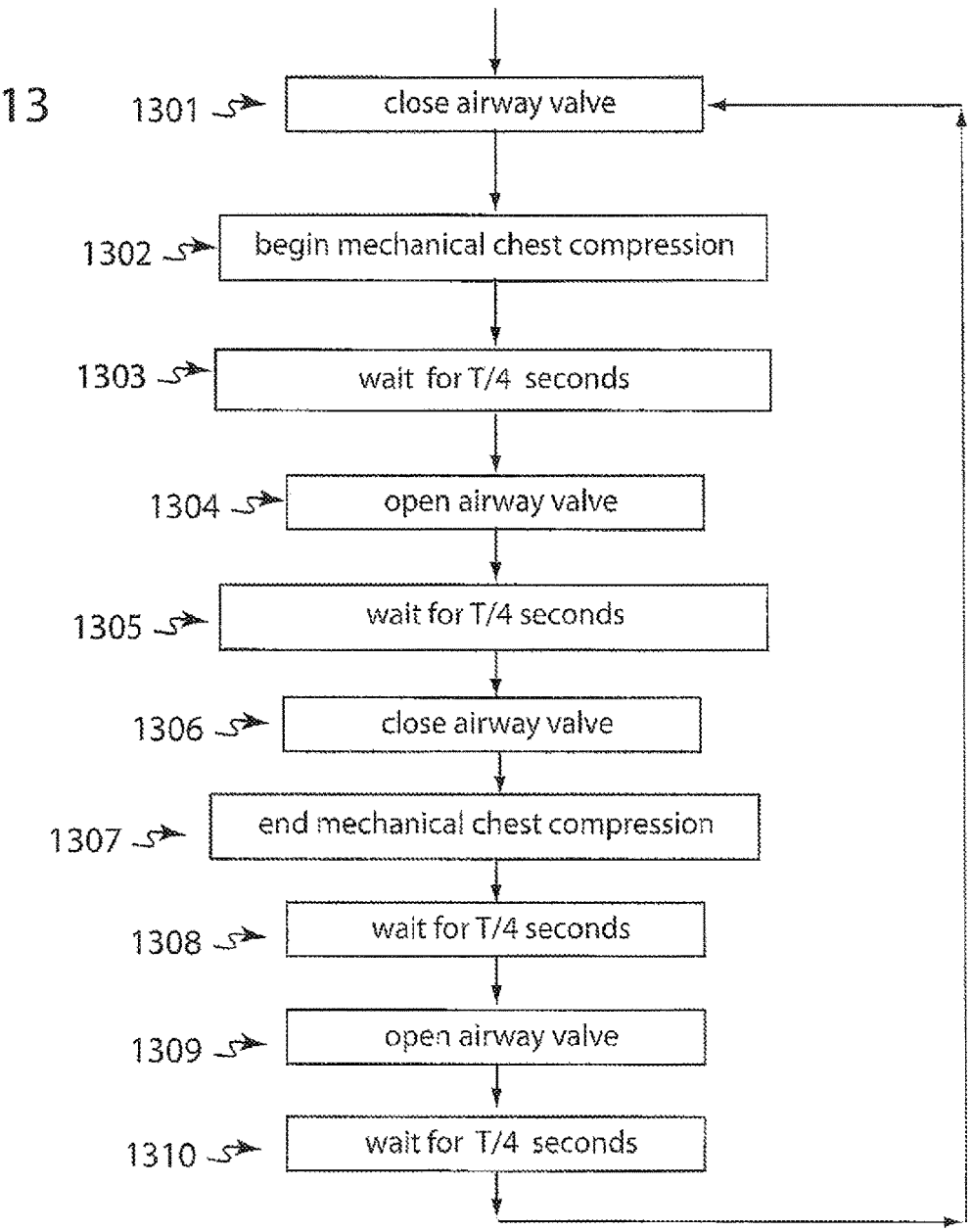
FIG. 13 shows a flow chart illustrating a control sequence used in an embodiment of the invention using a four state CPR cycle with regular cadence, the embodiment including a mechanical compression unit.

Referring now to FIG. 13 and FIG. 7, a description is given for the algorithm of a control unit 704 in an embodiment of this invention as shown in FIG. 7, described previously, but now using the four state timing of FIG. 11. FIG. 13 shows a flow chart representing a control sequence of a micro-controller or microprocessor included in a control unit 704 of the embodiment described in FIG. 7. The control sequence shown in FIG. 13 realizes the cardio pulmonary state sequence shown in FIG. 11 by properly activating valve 200 in synchrony with the information of compressions and decompressions delivered by compression unit 700 (FIG. 7). The control sequence begins at state 401 shown in FIG. 11, by having the control sequence at step 1301 with a closed airway valve. Next, the control unit 704 commands the mechanical compressor system of actuator 706 and plunger 708 to deliver a compression. Once the beginning of the first compression is effected in step 1302, control passes to 1303, a step in which a timer waits for an interval of T/4 (quarter of T) seconds, where T is a programmed CPR cycle period, a time interval of the duration of one compression and one decompression. A typical range of values for T could be 0.3 to 1.5 seconds, in accordance to known optimal compression rates, as is known in the art of CPR. For instance, T could be programmed to 0.6 seconds, corresponding to 100 compressions per minute. The programmed interval could be programmed once only at manufacture, or alternatively, be user programmable. The timer is preferably inherent to the microcontroller in control unit 704, but may also be external to it. In the next step 1304, the control unit 704 the airway valve 200 is opened, and in step 1305 a wait of T/4 seconds takes place. This occurs at time t4 504, marking the end of state 403 (FIG. 11), and control passes then to step 1306, in which the airway valve 200 is closed, and in step 1307, the compression is terminated. State 404 (FIG. 11) is then begun. Proceeding to the next control step 1308, said state 404 is held for a period of time T/4, until time t5 505 (FIG. 11). Control then passes to step 1309 in which the airway valve is opened, marking the beginning of state 405 (FIG. 11). Control then passes to step 1310, in which another delay interval of T/4 seconds is used, establishing the duration of state 405 (FIG. 11). After completing step 1310, control returns to the original step 1301, and the valve is closed in preparation for the next compression from the compression unit 700. In this way control continues as before, and the entire control sequence of FIG. 13 is repeated. It is understood that variations in the duration of the intervals described can still be present without departing from the scope of the invention.

In one improved embodiment of the invention, the duration of compression and decompression (as shown in FIG. 5 or FIG. 11) may be different. For example, the duration of compression might be one third of the total compression and decompression duration. Therefore, the decompression duration would be two thirds of said total. By having a longer decompression duration, the invention better resembles the natural beating of the normal heart, which has a shorter contraction (systole) duration as compared to the relaxation (diastole). This may provide further circulation enhancement benefits to the invention, because it better matches the time constants associated with blood circulation in the body.

In yet a further embodiment, and referring again to FIG. 7, the compression unit 700 includes a compression sensor (not shown) coupled mechanically to plunger 708 and electrically to control unit 704, to provide the knowledge to the microprocessor of when the compressions are actually occurring. This would allow for delays in the actual contact to the chest of the patient from the moment that a compression or decompression command is given by the control unit 704. In this embodiment, the implementation of the required steps to achieve the timing and enhancements described in FIG. 11 would be an obvious combination of the steps in FIG. 12 and FIG. 13, as will be apparent to those skilled in the firmware engineering arts.

Figure 14:
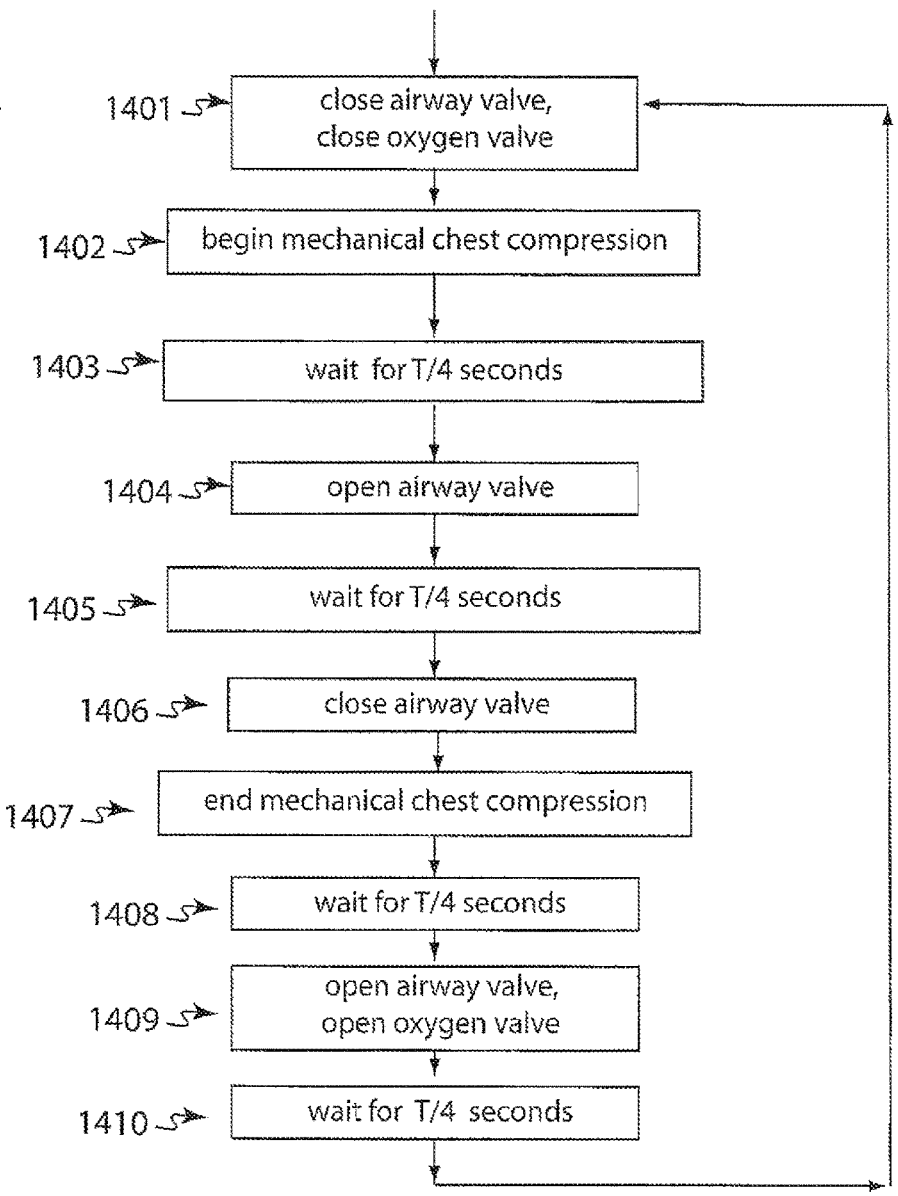
FIG. 14 shows a flow chart illustrating a control sequence used in an embodiment of the invention using a four state CPR cycle with regular cadence, the embodiment including a mechanical compression unit and oxygen delivery.

In a further embodiment of the invention, the previously described inventive apparatus of FIG. 9 can additionally include means to provide gases to the patient, such as oxygen, but instead of the five state timing of FIG. 5 the embodiment can use the four state timing of FIG. 11, described above. As such, FIG. 14 shows a flow chart representing a control sequence of a micro-controller or microprocessor included in a control unit 704 of the embodiment described in FIG. 9. The control sequence shown in FIG. 14 realizes the cardio pulmonary state sequence shown in FIG. 11 by properly activating valve 200 in synchrony with the information of compressions and decompressions delivered by compression unit 700 (FIG. 9). The control sequence begins at state 401 shown in FIG. 11, by having the control sequence at step 1401 with a closed airway valve 200 and a closed oxygen valve 906. Next, the control unit 704 commands the mechanical compressor system of actuator 706 to deliver a compression in step 1402. Once the beginning of the first compression is effected, control passes to 1403, a step in which a timer waits for an interval of T/4 (quarter of T) seconds, where T is the CPR cycle period time, as described above with respect to FIG. 13. In the next step 1404, the control unit 704 opens the airway valve 200 via valve actuator 202. This occurs at time t3 503 (FIG. 11). Control then passes to step 1405, where a wait of T/4 seconds elapses. This pause ends at time t4 504, marking the end of state 403 (FIG. 11), and control passes then to step 1406, in which the airway valve 200 is closed, and in step 1407, the compression is terminated. State 404 (FIG. 11) is then begun. Proceeding to the next control step 1408, said state 404 is held for a period of time T/4, until time t5 505 (FIG. 11). Control then passes to step 1409 in which the airway valve is opened, the oxygen valve is opened, marking the beginning of state 405 (FIG. 11) and permitting the ingress of oxygen into the patient. Control then passes to step 1410, in which another delay interval of T/4 seconds is used, establishing the duration of state 405 (FIG. 11). After completing step 1410, control returns to the original step 1401, and the airway valve 200 and oxygen valve 906 is closed in preparation for the next compression from the compression unit 700. In this way control continues as before, and the entire control sequence of FIG. 14 is repeated. It is understood that variations in the duration of the intervals described can still be present without departing from the scope of the invention.

In yet a further embodiment, and referring again to FIG. 9 and FIG. 7, the compression unit 700 includes a compression sensor (not shown) coupled mechanically to plunger 708 and electrically to control unit 704, to provide the knowledge to the microprocessor of when the compressions are actually occurring. This would allow for delays in the actual contact to the chest of the patient from the moment that a compression or decompression command is given by the control unit 704. In this embodiment, the implementation of the required steps to achieve the timing and enhancements described in FIG. 11 would be an obvious combination of the steps in FIG. 12 and FIG. 14, as will be apparent to those skilled in the firmware engineering arts.

Figure 15A:
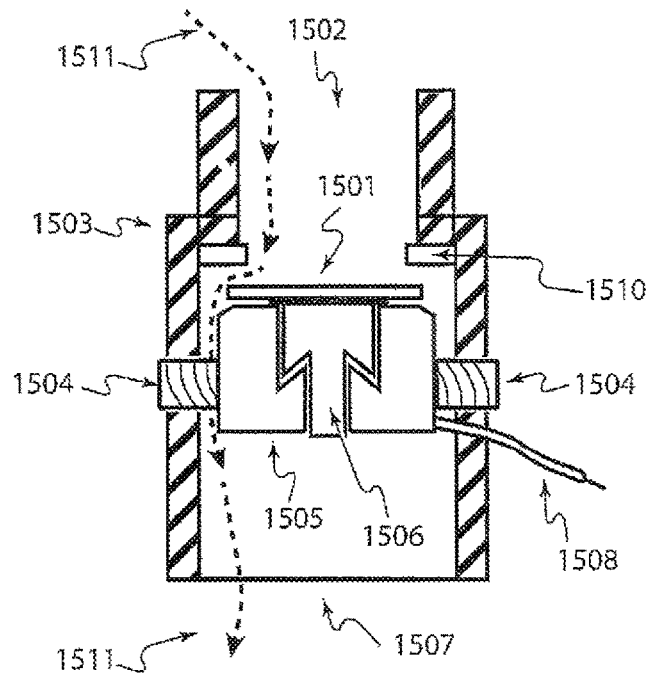
FIG. 15A shows an embodiment of an airway valve, in the open state.
Figure 15B:
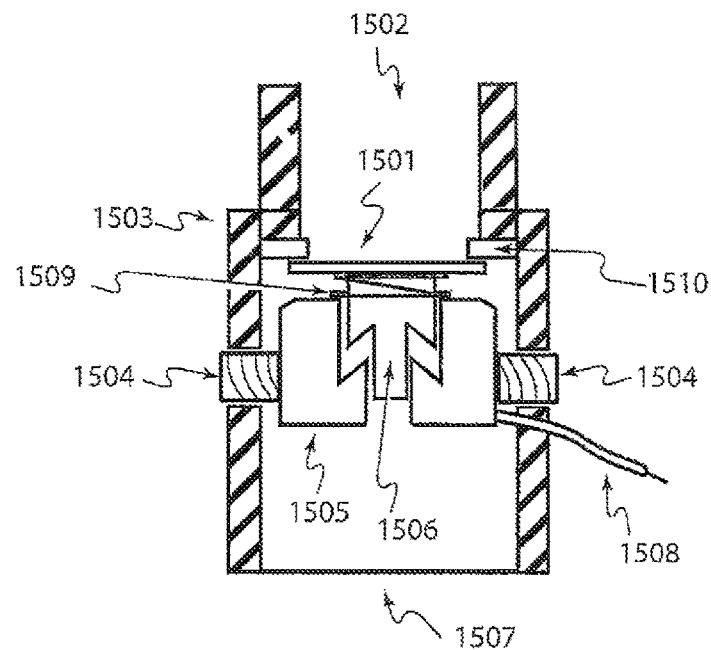
FIG. 15B shows an embodiment of an airway valve, in the closed state.

Referring now to FIG. 15A and FIG. 15B, the following paragraphs describe embodiments for an advantageous and practical airway valve 200. Such valve embodiments realize additional improvements beyond the electronic valves known in the art. Pneumatic valves have long been known in the art of air control. It is common to include a solenoid or other electromechanical device to actuate a flap or plunger that occludes an opening that permits the passage of air. A butterfly design is also well known in the art. Diaphragm mechanisms are also commonly used, where the diaphragm rests over an opening to occlude it, perhaps with a spring or elastic element acting on it. An active electromechanical mechanism as an actuator could then pull it away from the opening and uncover the opening permitting gas flow. However, while these kinds of designs enable the invention described in this document, they may be bulky, unreliable and not energy efficient. Further advantages in the invention would be realized if the valve 200 could be made as small as possible, with a minimal number of parts to enable high reliability and lower manufacturing complexity, and have features that are appropriate for emergency CPR situations. FIG. 15A and FIG. 15B show one such valve 200 in cross section. The same valve 200 embodiment can be seen in isometric view in FIG. 16. In FIG. 15A the valve is shown open, permitting the passage of respiratory gases 1511 in either direction. In this particular figure, the gases 1511 are shown flowing from the patient-proximal end 1502 towards the patient-distal end 1507. It is clear that the gases could similarly flow in the opposite direction. FIG. 15B shows the valve closed.

The valve body 1503 is constructed of a rigid, impact resistant and transparent plastic polymer, or similar material, and is shown with hatched pattern in the drawing. The transparency is important because it permits assessment of the patient's ventilation. For example, humidity in the patient's expiratory gases can appear on the inner surface of the valve body 1503. Transparency is also important to allow visualization of the valve state, which can be enhanced by adding a brightly colored section of the plunger 1506 that is easily discernible by the rescuer. Such colored section on the plunger 1506 can either appear or hide into and from the solenoid body 1505 as plunger moves. With the transparent construction of valve body 1503 this color will be easily visible. The transparency is also advantageous to visualize fluids or vomit that may appear in the valve during rescue.

Figure 16:
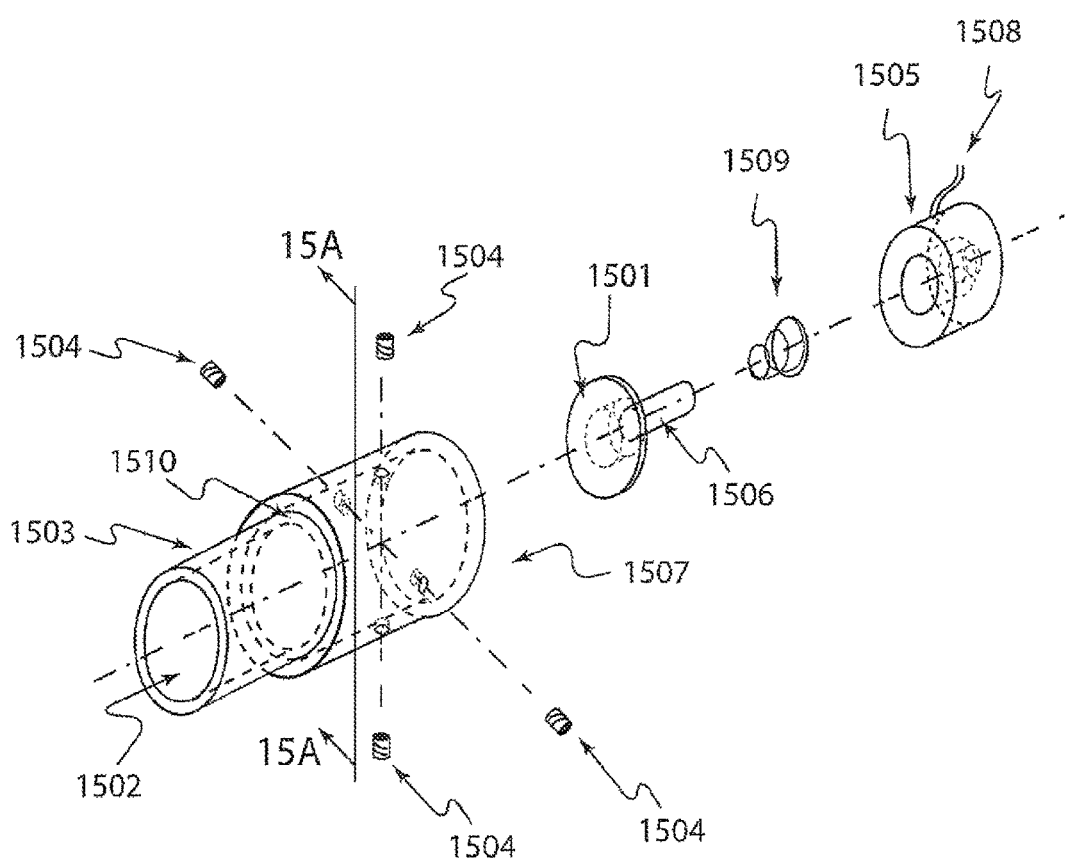
FIG. 16 shows an isometric view of the airway valve of FIGS. 15A and 15B.

The valve includes a plunger 1506 that, in a single piece, accomplishes the functions of: a) providing a ferromagnetic material that can be efficiently pulled by actuator solenoid 1505, and b) providing a smooth sealing surface 1501 that seals the opening seal 1510, thereby occluding the flow of gases. The plunger 1506 has a special shape, where it is thicker in diameter near the sealing surface 1501, and thinner in diameter towards the other end of the plunger 1506, opposite from the smooth surface 1501. A conical inner surface as shown in the cross section of plunger 1506 provides the transition from the larger diameter part to the smaller diameter part. This design of the plunger 1506, thus provides a single metallic piece that accomplishes sealing and ferromagnetic element function for the electromagnetic action of the valve. The design having a larger diameter and a smaller diameter permits a more efficient electromagnetic action, as there is more mass of ferromagnetic material for the same longitudinal distance of plunger, when compared to a solenoid that uses a single diameter plunger that is narrow. Thus, the embodiment shown in FIG. 15A, FIG. 15B, FIG. 16 allows a more compact activating mechanism that fits inside the valve body 1503, with no external parts outside of the valve body 1503. One embodiment of the valve is sized to commonly used diameters of connectors used in emergency medicine airway management. As such, patient-proximal end 1502 is sized with an inner diameter of 15 mm, and an outer diameter of 22 mm. Patient-distal end 1507 is sized with an inner diameter of 22 mm. Since it desirable to minimize dead space in emergency ventilation, minimizing the overall length of the valve—from the proximal to the distal end—is important. Given that the conventional diameters mentioned (15 and 22 mm) impose those dimensions to the construction of an airway valve 200, and since the length must be minimized, the plunger and solenoid design described above, with its electromagnetic efficiency and size reduction, is one that is particularly advantageous if size minimization and reliability is to be achieved, as is the case in CPR practice. Continuing now with the description of the airway valve 200 in FIG. 15A, FIG. 15B, and FIG. 16, small screws 1504 hold the solenoid 1505 centered in the lumen of valve body 1503, so that gases can flow around and through the solenoid 1505. Screws 1504 are recessed or flush with the external surface of valve body 1503, though they are shown—for clarity purposes—slightly prominent in FIG. 15A and FIG. 15B. A smaller number of screws (three, two, or even one), or other fixation structures could be used to hold solenoid 1505 in its centered place. Even a design with a total absence of screws could be used, for example by molding valve body 1503 to include supporting structures, by pressure fittings, or even adhesive mounting. However, and depending on whether the manufacturer wishes to minimize the cost of construction, or whether a cleanable valve 200 assembly is desired, the screws may provide an easier manner of disassembly. Solenoid 1505 has electromagnetic coils that can be energized via wires 1508, which may come out of the valve via substantially airtight openings. A second smooth sealing surface 1510 that is part of the valve body 1503 provides the opening and complementary seal against which smooth surface 1501 of the plunger 1506 acts to open and close the flow of gases. Smooth surface 1510 can be integral to valve body 1503, that is, of the same material and part of the same material block, so as to minimize the number of parts, and thereby improve reliability needed for CPR. A spring 1509 pushes the plunger 1506 and its smooth surface 1501 against the second smooth surface 1510, when the solenoid 1505 is not energized, as shown in FIG. 15B. This is a closed valve state. As can be seen in FIG. 16, the spring 1509 can be helical with diminishing diameter as it turns, so that when it is compressed by the electromagnetic action, (when the valve is open with an energized solenoid 1505), it provides a minimal amount of height of the compressed spring 1509, as shown in the open state in FIG. 15A. Minimizing the plunger travel distance, as well as the distances between plunger 1506 and solenoid 1505 all contribute to higher energy efficiency, which translates into smaller devices, and smaller batteries used in the total apparatus. These attributes are attractive for field emergency medicine, in cases when CPR must be applied for longer periods of time. In one embodiment a higher electric current can be applied to initially activate the solenoid and attract the plunger electromagnetically. Such higher energy may be needed to counteract differential gas pressures present across the valve, and to overcome the longer distance at which plunger 1506 is in the de-energized state from the solenoid 1505 center. Once the plunger 1506 is attracted and closest to the solenoid, the electric current delivered to the solenoid 1505 may be reduced, simply to maintain the valve open, while conserving energy. Lower energy is required because no differential pressures need to be overcome when the valve is open, and because the plunger 1506 is closest to the solenoid 1505.

In summary, for the valve 200 construction embodiments described, all the above elements of size reduction, part number reduction, combining an energy efficient solenoid and plunger design, along with simplification, helical spring design, energy delivery result in a smaller and more reliable system, while fulfilling ventilation and fluid assessment requirements with the use of transparent materials.

Figure 17A:
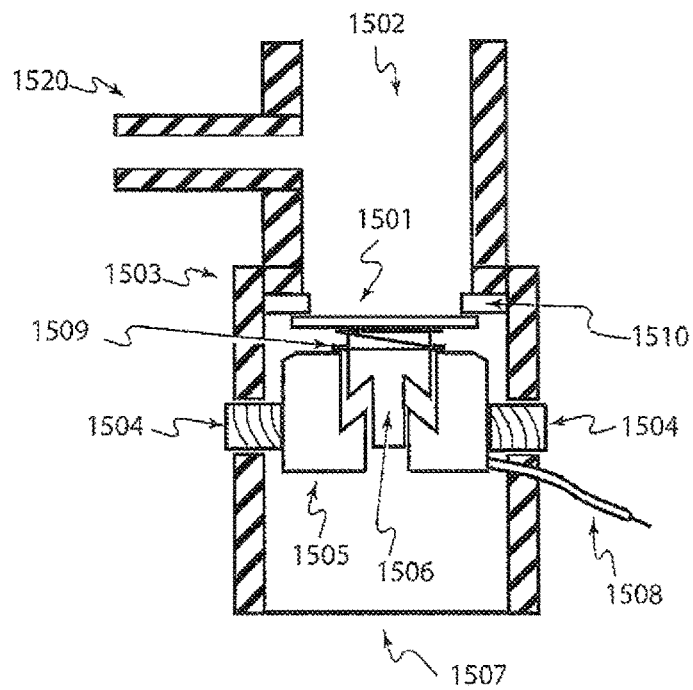
FIG. 17A shows an embodiment of an airway valve, with a gas port at the end of the valve proximal to the patient.
Figure 17B:
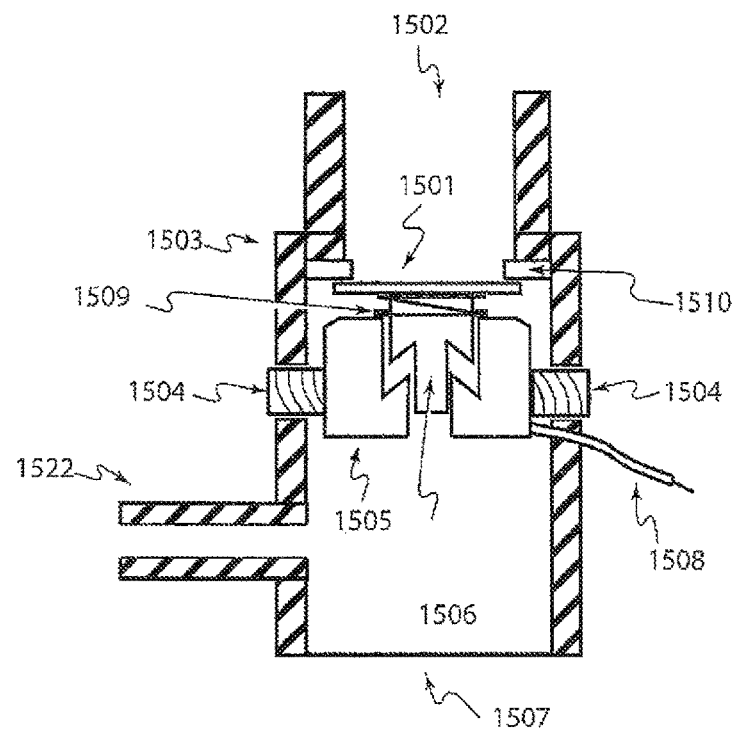
FIG. 17B shows an embodiment of an airway valve, with a gas port at the end of the valve distal to the patient.

Referring now to FIG. 17A and FIG. 17B, further embodiments of airway valve 200 are shown that include a proximal gas port 1520 at the patient proximal end of the valve (FIG. 17A), or at the patient-distal end of the valve (distal gas port 1522 in FIG. 17B). These ports can be used to deliver respiratory gases as shown in FIG. 9, and described in the corresponding description in this document. Specifically, in the description for FIG. 9, both active and passive oxygen delivery was described. For active oxygen or respiratory gas delivery, a valve such as shown in FIG. 17A is used, and port 1520 is used to inject an oxygen gas mixture during state 405 of the inventive sequence of the invention, as previously described. The valve of FIG. 17A can be closed during such active oxygen delivery, so that a positive pressure oxygen delivery results, a kind of forced inflation, with a pressure similar to that of conventional bag ventilation, or mechanical ventilation conventionally used in emergency and critical care medicine. Note that the active oxygen delivery could be delivered deeper into the trachea via a port on an endotracheal tube connected to patient-proximal end 1502 of the valve. Such endotracheal tube port would obviate the need for patient-proximal port 1520, and so the valve embodied in FIG. 15A, 15B and FIG. 16 would better be used in that rescue scenario. Alternatively, the valve of FIG. 17A can be open during the sequence state 405, and oxygen flowing through port 1520 would be passively inhaled into the patient's lungs via patient-proximal end 1502. For passive oxygen delivery, the valve embodiment of FIG. 17B can be used, with the oxygen gas mixture delivered via patient-distal port 1522. One advantage of this type of embodiment is that a simpler oxygen system can be used by the rescuer, simply providing a continuous flow of oxygen, that is passively inhaled by the patient during sequence state 405, but otherwise vented to atmosphere at all other times. If the oxygen control described in FIG. 9 is used, then oxygen valve 906 only needs to be open during the state 405, and oxygen can be better conserved. So there is a tradeoff between system simplicity and oxygen savings, and the invention described in this document will operate in both cases. Ports 1520 and 1522 can be angled with respect to the longitudinal axis of valve body 1503 so that the stream of respiratory gases can be directed more towards the patient and thereby increase the efficiency of passive oxygen delivery. Other uses for port 1520 and 1522 include sampling of expiratory gases, such as end tidal carbon dioxide, as is conventional in CPR airway devices and practice.

In closing, a description has been given of a CPR device and method that provides enhanced circulation by an optimal combination and sequencing of maximal positive and maximal negative intrathoracic pressures, while maintaining a degree of passive ventilation to the patient. Namely, the embodiments of the invention provide for an optimal positive thoracic pressure compression state 401, with passively or actively filled lungs, achieved by either passive chest recoil with an open airway as via state 405, or an active inflation mechanism. Said embodiments also provide for an optimal negative pressure decompression state 404, combined with actively emptied lungs (by chest compression). Further the embodiments provide for the appropriately ordered states 401, 404, and 405 that enable the optimal pressure states and open airway ventilation state of the cardio pulmonary system during repetitive CPR. Further, the embodiments include intervening states 402 and 403 that correctly set up the previously mentioned states 401, 404, and 405, by ensuring the best lung inflation level for those states. Embodiments with a five state, pump-pump-pause compression cadence were described. A four state embodiment without state 402, yielding a regular compression cadence was also described. Variations of the invention are possible, with additional intervening states not described here, but in any case preserving the three basic states 401, 404, and 405 in that order, without departing from the scope of the invention.

Embodiments that, in their CPR cycles, include repetitive subsequences of the above states are also possible with this invention, while in total the cycles form the overall 4 or 5 state sequence of this invention. For example, the invention could operate by having a subsequence (e.g. 1 to 10 cycles), of chest compression and decompression with closed airway, (states 401 and 402) followed by a state of chest compression with open airway to ventilate gas from the lungs (state 403), then followed by a subsequence, (e.g. 1 to 10 cycles), of chest compressions and decompressions with closed airway (state 404), then followed by a state 405 of open airway and chest decompression to admit gas into the lungs of the patient, as discussed previously. Such last state 405, as was also described previously, can also be enabled by a closed airway valve with an oxygen source (state 405), to achieve active oxygen inspiration.

Furthermore, the embodiments described above could be combined with ventilator machines, or combinations of ventilator and automatic CPR machines. In this case positive thoracic pressure providing greater degrees of air inflow in state 405 in FIG. 5 or FIG. 11 would be possible, without departing from the scope of the invention.

In one embodiment, an apparatus of the present invention may include sealing means to control the airway of the patient 102; a valve 200 that in combination with the sealing means is configured to open and close the airway of the patient 102; means to deliver mechanical compressions to the chest; means to actuate the valve 200; and a control unit 204 which is coupled to the valve actuating means 202 and mechanical compression delivery means. As will be appreciated by one skilled in the art, the patient's chest may include a phase of compression and a phase of decompression. The control unit 204 is configured to actuate the valve 200 to affect a sequence of states including a decompressed chest and open airway to let respiratory gas into the lungs, compressed chest with closed airway, and compressed chest with open airway to let respiratory gas out of the lungs. Accordingly, the present invention provides the benefit of the control unit 204 actuating the airway valve 200 to open or close partway through a compression or a decompression. As discussed above and below, this feature assists in sequences and states that positively influence circulation of the patient 102.

Moreover, the sequence of states may further include a decompressed chest with a closed airway after the compressed chest with an open airway to let respiratory gas out of the lungs. This sequence has the effect of providing both an inspiration and expiration in single compression and decompression cycle. However, as one skilled in the art will appreciate, in some embodiments of the present invention, the ratio of expirations to inspirations may be other than one to one. For example, the ratio of expirations to inspirations may be higher, such as two to one through ten to one. As will be discussed in further detail below, some embodiments of the invention may include an oxygen source. Oxygen may be provided at any concentration, but preferably 100% oxygen will be delivered to the patient 102. Because the atmosphere's air only includes about 21% oxygen, an inspiration of 100% oxygen yields more oxygen transport per respiratory cycle than that at atmospheric air. In contrast, carbon dioxide, which is removed from the body at each expiration, cannot be removed at higher rates or concentrations than those present in the body. Hence, the possibility of fewer inspirations per expiration to support vital oxygen and carbon dioxide transport when ventilating using high concentrations of oxygen such as 100%. While any ratio of expirations to inspirations may be used without departing from the scope of the invention, as discussed above, ratios of one to one through ten to one are preferred.

Furthermore, in another embodiment of the present invention, after the state of a compressed chest with an open airway to let respiratory gas out of said lungs, the following states may occur: (1) decompressed chest with closed airway; (2) compressed chest with closed airway; and (3) compressed chest with open airway to let respiratory gas out of the lungs. Moreover, the above described cycle may be repeated prior to an inspiration. As discussed above the ratio of expiration to inspiration may be greater than one to one. For example, these three states may be repeated anywhere from three to eight times prior to an inspiration, providing for ratios up to 10 expirations to 1 inspiration.

As provided in further detail above, a phase of compression may be caused by a manual compression and/or a mechanical compression. Moreover, a phase of decompression may be caused by passive decompression and/or active decompression.

A control unit of the present invention may be of any means known in the art now or in the future, although embodiments including a microprocessor or microcontroller are preferred, as discussed above. Moreover, an apparatus of the present invention may include means for sensing or detecting compressions and decompressions. Further, an apparatus of the present invention may include means for delivering mechanical compressions and/or decompressions to the patient 102. In one embodiment of the present invention the control unit 204 may actuate the airway valve 200 to open or close at a point in time that is between 10% to 90% of the time interval of a compression or between 10% to 90% of the time interval of a decompression. In further embodiments, the control unit 204 may actuate the airway valve 200 to open or close at a point in time that is between 20% to 80% of the time interval of a compression or between 20% to 80% of the time interval of a decompression. Furthermore, the control unit 204 of the present invention may further actuate the airway valve 200 to open or close at the beginning of a chest compression, the end of a chest compression, the beginning of a chest decompression, and/or the end of a chest decompression.

Accordingly, a method of the present invention may include sealing the airway of a patient with sealing means, as discussed in further detail above. A rescuer 100 may further provide a valve 200 that works in combination with the sealing means to open and close the airway of the patient 102. Further, the valve 200 may include a valve actuating means 202. The rescuer 100 may further provide a control unit 204 that is coupled to the valve actuating means 202 to provide ventilation to the patient 100. The control unit 204 may be configured to synchronize ventilation with at least one of a compression or decompression of the patient 100. Moreover, the control unit 204 may actuate the valve 200 to open or close at a point in time that is after the start of a chest compression but before the end of a chest compression and/or after the beginning of a chest decompression but before the end of a decompression. Moreover, the control unit 204 may further actuate the valve 200 to open or close at the beginning of a chest compression, the end of a chest compression, the beginning of a chest decompression, and/or the end of a chest decompression.

A further method of the present invention may include sealing the airway of the patient, providing a valve that in combination with a sealing means is configured to open and close the airway of the patient, providing means to actuate the valve, and providing a control unit coupled the valve actuating means. The control unit is configured to actuate the valve to effect the following sequence of states: (1) decompressed chest an oxygen valve to let respiratory gas into the lungs, (2) compressed chest with a closed airway, and (3) compressed chest with an open airway to let respiratory gas out of the lungs. In another embodiment, a method of the present invention may include further providing an oxygen source to deliver oxygen to the patient, with the oxygen source having an oxygen valve and an oxygen valve actuator.

Although preferred sequences of inspirations, expirations, compressions, and decompressions are provided herein, it is anticipated that any sequence may be used without departing from the scope of the invention. The provided sequences create the benefit of hemodynamic improvement via positive intrathoracic pressure or negative intrathoracic pressure (vacuum), as discussed in greater detail above. However, it is anticipated that ventilation may occur without synchronizing ventilation, including both inspirations and expirations, to chest compression and decompression, and in turn positive and negative intrathoracic pressures, so as to provide the hemodynamic benefits discussed above. Moreover, a sequence of the present invention could have the hemodynamic benefit of only one of positive or negative intrathoracic pressure without departing from the scope of the present invention.

Advantageously, certain embodiments of the present invention provide a hands free means of CPR, with no hands required to provide compressions or ventilations. Moreover, embodiments of the present invention may provide inspirations to the patient 102 during the decompression phase only, thus reducing or eliminating completely the inefficiency and high lung pressures of providing an inspiration to the patient during a chest compression. Furthermore, embodiments of the present invention provide for smaller ventilations, or microventilations to be given continuously as part of the CPR method, without larger ventilations given with bags, for example, 10 times a minute. As such, in some embodiments, those smaller inspirations may be given more often than with prior CPR and ventilation devices and methods. Although ventilations of the present invention may be provided at any pressure and volume, it is preferred that each delivers approximately 50-150 milliliters of oxygen are provided. Accordingly, benefits of the present invention may include conservation of oxygen and use of smaller oxygen tanks that may be more portable than those currently used.

Embodiments of the present invention may include an oxygen source. The oxygen may be delivered via passive or active ventilation, which are both described in further detail above. As will be appreciated by one skilled in the art, the location of the oxygen delivery jet 916 will vary depending on whether passive or active ventilation is employed. In active ventilation, the oxygen jet 916 may be located between the patient's 102 lungs 212 and the airway valve 200. In this circumstance, in order to allow oxygen to enter the patient's lungs, the airway valve must close as the oxygen valve is opened. Alternatively, in passive ventilation, the oxygen jet 916 is located in front of the airway valve 200, as seen in FIG. 9, and not in between lungs and airway valve. In this circumstance, in order to allow oxygen to enter the patient's lungs, the airway valve 200 must open to allow air to reach the patient's lungs. Accordingly, as one skilled in the art will appreciate, and as discussed in further detail above, the timing of the opening and closing of the airway valve 200 will vary depending on whether active or passive ventilation is used.

Figure 18A:
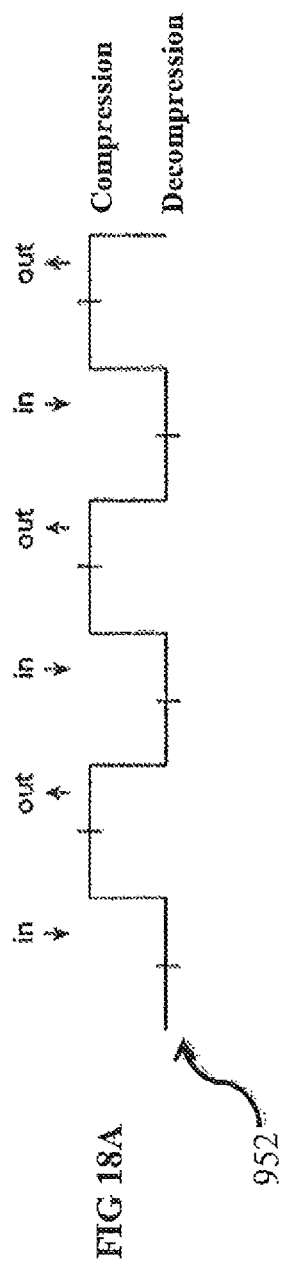
FIG. 18A is a schematic illustrating the sequence of compressions, decompressions, inspirations, and expirations of FIG. 11 in accordance with one or more examples of the present invention.

As discussed above and provided in FIG. 5, an exemplary sequence of the present invention may include (1) compressed chest with closed airway; (2) decompressed chest with closed airway; (3) compressed chest with open airway to ventilate respiratory gas out of the patient's 102 lungs 212; (4) decompressed chest with closed airway; and (5) decompressed chest with open airway to ventilate respiratory gas into the patient's 102 lungs 212. Furthermore, as discussed above and provided in FIGS. 11 and 18A, a second exemplary sequence 952 of the present invention may include (1) compressed chest with closed airway; (2) compressed chest with open airway to ventilate respiratory gas out of the patient's 102 lungs 212; (3) decompressed chest with closed airway; and (4) decompressed chest with open airway to ventilate respiratory gas into the patient's lungs 212.

Figure 18B:
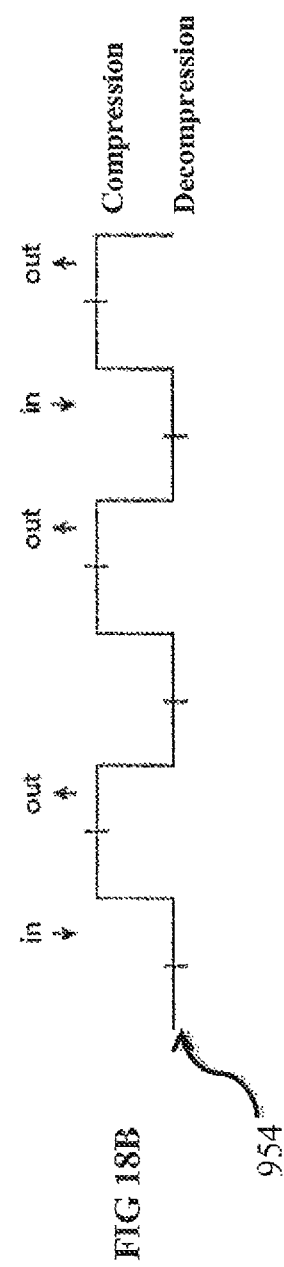
FIG. 18B is a schematic illustrating another sequence of compressions, decompressions, inspirations, and expirations in accordance with one or more examples of the present invention.
Figure 18C:
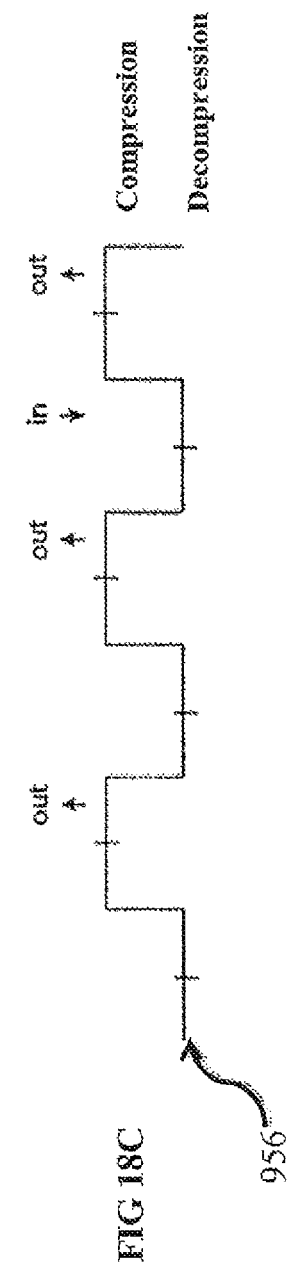
FIG. 18C is a schematic illustrating yet another sequence of compressions, decompressions, inspirations, and expirations in accordance with one or more examples of the present invention.

Further illustrating the sequences discussed above, FIGS. 18B and 18C provide third 954 and fourth 956 exemplary sequences of the present invention, respectively. In the third exemplary sequence 954 of FIG. 18B, which provides for a ratio of two expirations to one inspiration, the sequence of states includes: (1) decompressed chest with open airway to ventilate respiratory gas into the patient's 102 lungs 212; (2) compressed chest with closed airway; (3) compressed chest with open airway to ventilate respiratory gas out of the patient's 102 lungs 212; (4) decompressed chest with closed airway; (5) compressed chest with closed airway; (6) compressed chest with open airway to ventilate respiratory gas out of the patient's 102 lungs 212; and (7) decompressed chest with closed airway. In the fourth exemplary sequence 956 of FIG. 18C, which provides for a ratio of three expirations to one inspiration, the sequence of states includes (1) decompressed chest with open airway to ventilate respiratory gas into the patient's 102 lungs 212; (2) compressed chest with closed airway; (3) compressed chest with open airway to ventilate respiratory gas out of the patient's 102 lungs 212; (4) decompressed chest with closed airway; (5) compressed chest with closed airway; (6) compressed chest with open airway to ventilate respiratory gas out of the patient's 102 lungs 212; (7) decompressed chest with closed airway; (8) compressed chest with closed airway; (9) compressed chest with open airway to ventilate respiratory gas out of the patient's 102 lungs 212; and (10) decompressed chest with closed airway. However, it is anticipated that any number of sequences may be used without departing from the scope of the invention.

Figure 19:
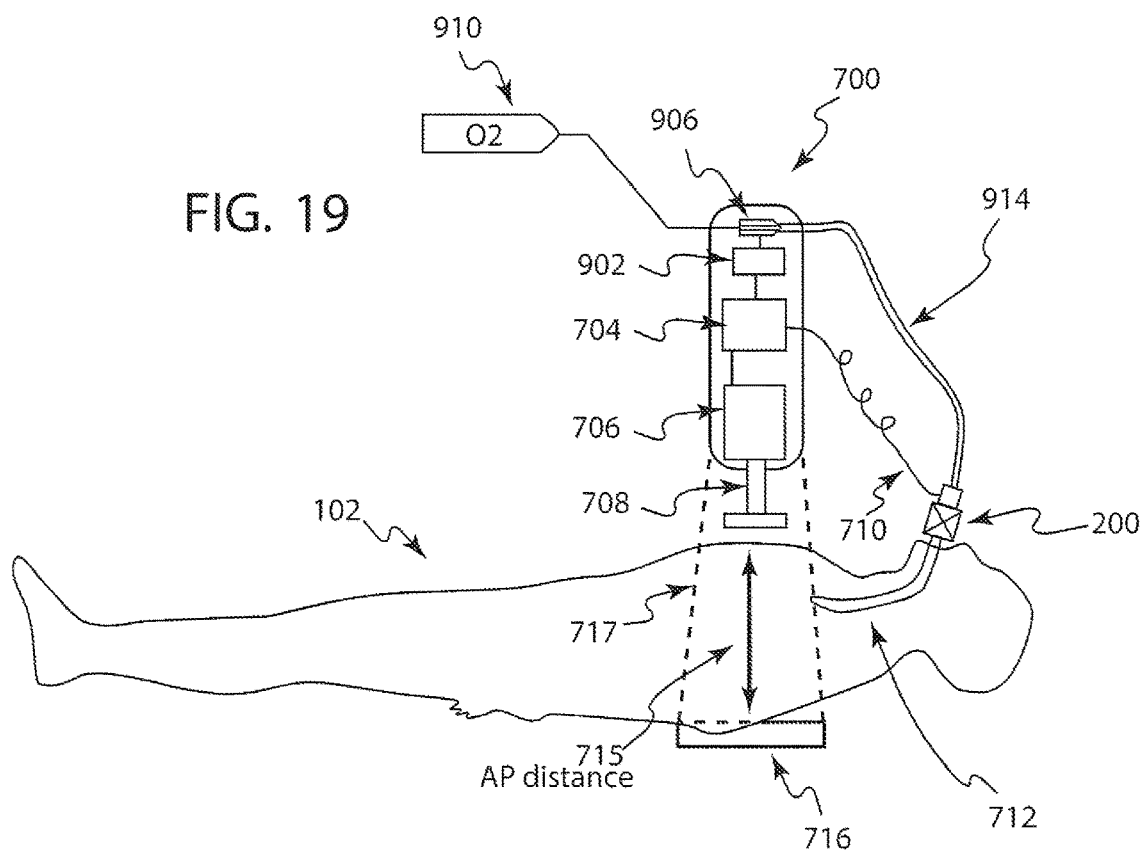
FIG. 19 shows an embodiment of the invention including a backplate which may be used in measuring an anterior to posterior distance of the patient.

FIG. 19 shows the invention as was described in FIG. 9 and FIG. 7 previously, and adds other inventive aspects relative to ventilation. Backplate 716 in FIG. 19 is commonly provided in prior art mechanical chest compressors (such as that of U.S. Pat. No. 7,226,427 to Steen, previously cited). Backplate 716 may support unit 700 via an arm 717, which may keep the compression unit in a fixed geometry when compressions are delivered, and thereby allow the appropriate forces to compress the chest of patient 102. Some conventional mechanical chest compression devices also include two arms 717, (e.g., one on either side of the thorax of patient 102), to support unit 700. This geometrical disposition can be advantageously used with additional features of the present invention to provide automation and solve a common problem during mechanical ventilation of patients in emergency situations. Specifically, when rescuers apply a ventilator to a patient during cardiopulmonary resuscitation, they may need to manually adjust the ventilator's tidal volume. As is known in the art, tidal volume is the quantity of gas injected into the patient in each breath.

The tidal volume setting depends on the patient's weight. Such is a subject of a medical journal publication entitled "Arterial blood gases with 700 ml tidal volumes during out-of-hospital CPR" by Dorph, Wik and Steen, published in the journal Resuscitation, volume 61 of 2004, pages 23-27. In that publication, a volume of 10 milli-Liters (mL) of oxygen per kilogram of patient weight is recommended for intermittent positive pressure ventilation at a rate of 12 breaths per minute. Other types of ventilation may use different tidal volumes: for example 2.5 mL per kilogram. It will be understood that the device and methods of the present invention may employ any effective tidal volume desired. Furthermore, it is common for rescuers to estimate the weight of the patient and use it to manually adjust the tidal volume that a mechanical ventilator will use. This procedure has several disadvantages. First, estimating and adjusting the tidal volume is time-consuming in a situation of emergency where seconds count. Second, estimating the weight of the patient by eye, especially in an emergent situation, is not a very accurate process. Third, it is desirable to minimize the hardware associated with tidal volume adjustment. This is because the equipment carried by rescuers should preferably be lightweight and small.

An inventive solution that eliminates the above issues follows. Instead of weight, the anterior-posterior (AP) distance 715 of the patient's chest can be used to set the ventilation tidal volume or maximum airway pressure setting. Because compressor unit 700 includes a control unit 704 that controls actuator 706 and plunger 708, the unit 700 can know the distance between the plunger's bottom 708 and back plate 716. When unit 700 is first applied to patient 102, the plunger 708 moves from its retracted or stowed position to the starting position where it contacts the patient's chest. This occurs just before the initiation of CPR compressions. Such starting position is the anterior-posterior (AP) distance 715. As an example, a microprocessor in unit 704 may contain a memory register that keeps said AP distance value, which it can determine from the positioning commands it gives to actuator 706. These position commands and motion variables are well-known in the arts of actuators controlled by electric motors, for example.

To illustrate a typical instance, the stowed position of plunger 708 is 30 centimeters, measured from backplate 716. Once the unit 700 is applied to the patient 102, the plunger 708 may move 5 centimeters to come in contact with the patient's chest. Therefore an anterior-posterior (AP) distance of 25 cm is determined by subtracting 30 minus 5, as both quantities are known to control unit 704. The control unit 704 can use said AP distance to estimate a patient weight and set a tidal volume or maximum airway pressure setting. For example, a large person can have an AP distance of 26 cm. A medium-sized person can have an AP distance of 20 cm. And a smaller person can have an AP distance of 15 cm. Typical weights for large, medium, and small sized persons are 100, 70 and 50 kilograms, respectively. Control unit 704 can then use these values with a pre-set tidal volume per kilogram (for example 2.5 mL/Kg) to determine the tidal volume to be delivered. In the 3 sizes described, and using weight as a guide, this would correspond to tidal volumes of 250, 175, and 125 mL, respectively. An equation that is contained in control unit 704 can be used to convert from AP distance to tidal volume. For instance, using a linear fit to the tidal volume versus AP data given above, an equation of Tidal Volume=(AP×12.5)−66.67 is determined (with units of AP in centimeters, and tidal volume in mL). Other fits, such as polynomial fits could be used instead, as is known in the engineering arts. A similar equation could be determined for such fit.

In this way, the determination of tidal volume is automated, accurate, and simply determined based on the anterior-posterior distance 715 that is automatically calculated when unit 700 is applied to the patient.

To deliver the tidal volumes determined above in accordance with the inventive timing described in this document (e.g., as in FIG. 5, FIG. 11, or FIG. 18), control unit 704 in FIG. 19 activates valve 906 through actuator 902 so that oxygen (or other respiratory gas) from source 910 flows to patient 102 via line 914 to airway valve 200, which can be coupled to line 914 as described previously in FIG. 17. Alternatively, line 914 can be coupled to an endotracheal tube or other airway device.

Variations of the above compression unit are possible without departing from the scope of this invention. For example, the oxygen valve 906 and oxygen valve actuator 902 may be located outside the compression unit 700, as shown in FIG. 9. In another example, instead of a plunger, a mechanical chest compressor using a band surrounding the thorax to compress the chest could be used. An instance of one such device is the Autopulse™ device manufactured by Zoll Medical. Another is the Weil™ Mini Chest Compressor manufactured by Resuscitation International. When embodied with a band chest compressor, the invention uses the band's perimeter instead of the AP distance to determine the tidal volume. As before, the band perimeter, (taken before the compressions begin, for example), provides a patient size to the control unit 104 that can be used by the invention to determine tidal volumes automatically.

The following paragraphs describe improved embodiments of the invention that incorporate airway pressure monitoring to further automate the ventilation and circulation. In this way, the rescuer is relieved from keeping track of this information during an emergency. Such automation is realized in one embodiment by using preset airway pressure targets and ranges, automatic adjustments to tidal volume, and the automatic method of setting an initial tidal volume as described previously. Below, embodiments are described that simplify and further optimize the hardware of the invention.

Figure 20A:
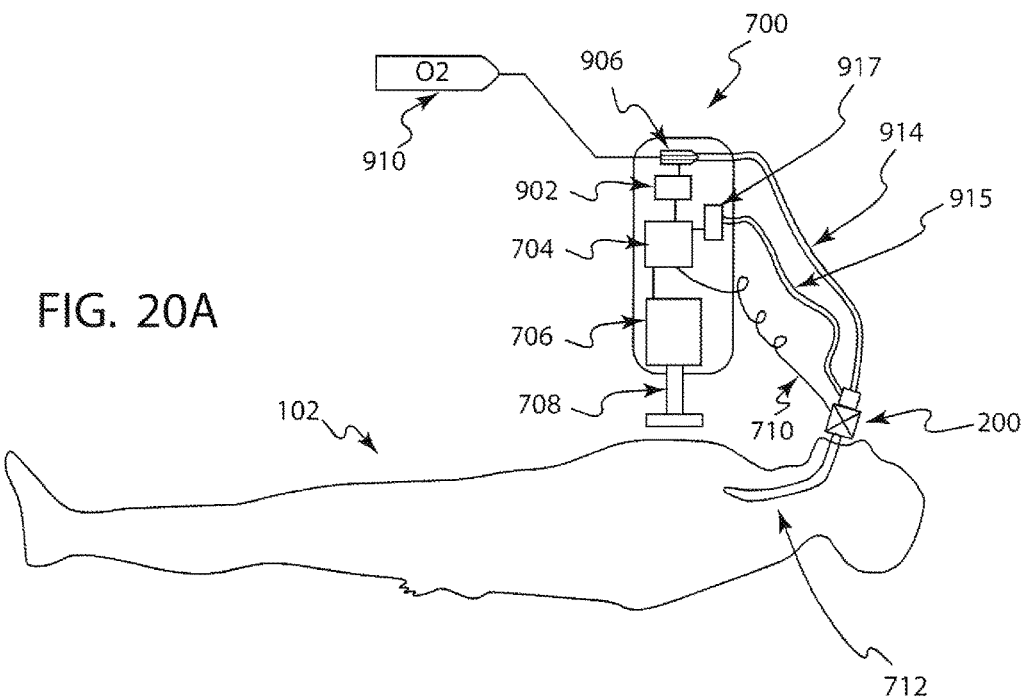
FIG. 20A shows an embodiment of the invention including airway pressure monitoring means.

One embodiment to provide improved automation is shown in FIG. 20A. Control unit 704 monitors airway pressure via a line 915 (e.g., a plastic tube) that provides a volume of gas, which communicates the airway gas space (near the patient at valve 200 or in an endotracheal tube, for example) with a pressure transducer 917. The pressure transducer 917 is coupled to control unit 704 which may include an analog to digital converter to convert the airway pressure signal to a digital value. It can then be used by control unit 704 to automatically adjust the amount of oxygen delivered to the patient by controlling oxygen valve 906 via actuator 902.

One exemplary algorithm for automation implemented in control unit 704 determines, in a first step, the appropriate default tidal volume to use based on the AP distance, as was explained previously above. In a cited example, 125 mL of oxygen is required when the patient's AP distance is 15 cm. Second, when a rescuer operating unit 700 presses a button (not shown) that commands control unit 704 to begin the CPR procedure, unit 700 begins compressing and decompressing the chest of patient 102, and control unit 704 operates the oxygen valve 906 and airway valve 200 in accordance to the sequences of FIG. 5, FIG. 11. The system will initially use the automatically determined tidal volume when injecting oxygen, as described in the first step above. In another embodiment of the algorithm, control would proceed as described above except that the airway pressure to be used would be that of state 405 (shown in FIG. 5 and FIG. 11). In one particular embodiment, the terminal airway pressure towards the end of this state 405, (e.g., average or median of the last 40 milliseconds) gives an indication of the degree of ventilation filling that is achieved with the oxygen injection of said state, before chest compression begins. In another embodiment both pressures in combination, (that is, that of state 401 and that of state 405) would be used to control oxygen injection. Since the pressure at the end of state 405 depends on the degree of decompression of the chest (for example, by varying active decompression), such combined control permits a management of ventilation that includes both aspects of the compression decompression cycle. For example if the terminal airway pressure of state 405 is too high, the quantity of oxygen injection may be reduced. In one embodiment, the monitoring of airway pressure at the end of decompression can be used to ascertain whether an active decompression function is operating properly. Normally this function is provided by a suction cup applied to the chest of patient 102, as described in the Steen U.S. Pat. No. 7,226,427 cited earlier. If the patient cup is misplaced or if there is too much hair on the chest, or if the chest is too concave, adequate active decompression may not be possible because the suction cup is unable to properly secure and pull the chest surface. This would be detected by control unit 704 as an increase in the terminal pressure of state 405. Control unit 704 may then provide an alarm to the rescuer to correct the suction cup placement, and may adjust the quantity of oxygen injected for example by reducing it to avoid excessive pressures in state 401. The threshold pressure to trigger an alarm could be preset within the memory of control unit 704, or could be a value obtained by control unit 704 during the initial set up of the device on the patient. A typical threshold value could be in the range of 0 to 40 cm of water.

Third, as CPR proceeds, control unit 704 monitors the peak positive airway pressure of state 401 (shown in FIG. 5 and FIG. 11). If a corresponding low pressure is detected via transducer 917, (for example, in one embodiment below a preset value of 10 cm of water), control unit 704 may adjust the oxygen injection quantity delivered at the appropriate time in the sequence it is controlling. Thus, control unit 704 can increase oxygen delivery in state 405 (shown in FIG. 5 and FIG. 11) by opening valve 906 to a greater extent (as with a proportional valve). Alternatively, it can increase oxygen delivery by extending the duration of opening of valve 906 during state 405. Moreover, a second valve disposed in parallel to valve 906 could also be used to increase the amount of oxygen, as is known in mechanical ventilation engineering. The adjustment can be controlled by gradually incrementing oxygen delivery over several compressions (for example, over 2 to 20 compressions) while monitoring the peak airway pressure at state 401 of the sequence. Once the preset pressure target is reached, (for example, in a range from 5 to 40 centimeters of water), the gradual increments of oxygen stop and its oxygen injection is kept at a constant quantity. In a similar manner, an airway pressure that is too high during state 401 would similarly be controlled by decrementing the quantity of oxygen delivered during state 405. Maintaining a particular pressure value using corrective increments derived from a monitored value of the said pressure is known in the art of control engineering. For example, a proportional integral derivative control algorithm (PID) could be used. Other known control methods could be used without departing from the scope of the invention.

The coupling of lines 914 and 915 to the patient's airway valve 200 can occur in several ways. A valve such as that described in FIG. 17A could be used. A similar valve 200 is shown with further improvements in FIG. 20B. In this embodiment, line 914 delivering oxygen may connect to port 1520, and pressure monitoring line 915 may connect to port 1521 to sample the airway pressure at patient-proximal end 1502. The drawing shows the ports disposed longitudinally, but they could be placed at the same cross sectional level or anywhere else as long they communicate with the gas space of the patient-proximal end 1502. Port 1520 may optionally include an angle 1524 of approximately 60 to 90 degrees as the port enters the space near the patient-proximal end 1502, so that oxygen jet 916 is directed deeper into it airway of the patient, thereby improving respiratory gas exchange. In another embodiment, after it enters port 1520, the flow of oxygen may be directed deeper into the patient with a tube extension (not shown) that follows the turn of angle 1524. In one embodiment, such an extension could be implemented by a first lumen in an endotracheal tube 712, and be dedicated solely to oxygen delivery. A second lumen in endotracheal tube 712 would then be used to exhale respiratory gases from the patient. In this way oxygen jet 916 can be delivered closer to the lungs of the patient, improving ventilation gas exchange. These techniques of delivering oxygen deeper into the trachea of the patient are known in the arts of medical ventilation. One exemplary endotracheal tube that accomplishes this function is the Boussignac tube. It will be understood to those in the art, that the invention could also operate if this port 1520 is not present in airway valve 200 of FIG. 20B and instead is part of an endotracheal tube such as a Boussignac tube.

Airway pressure monitoring may also be obtained by connecting pressure monitoring line 915 to a tracheal tube 712 or other similar airway device that includes a port that allows airway pressure monitoring. An airway valve 200 without port 1521 would be used in that case, or a cap could be placed to seal the port. Yet another manner of obtaining airway pressure is to include the pressure transducer 917 and even its signal conditioning at the airway valve 200. In this case line 915 would be communicating pressure to control unit 704 not through a volume of gas in a lumen, but by electrical signals in wires substituting line 915, or bundled with conductors 710.

Turning to a hardware simplification aspect of the invention, an embodiment includes the combination of line 914, line 915, and electric conductors 710 into a more compact bundle. One such embodiment is bundled tube 2013, shown in cross section in FIG. 20C. This may reduce the clutter of wires and pneumatic lines that may hinder the rescue efforts. This embodiment uses a dual lumen plastic tube 2013, with a first lumen 2014 providing the oxygen injection function of line 914, and a second lumen 2015 combining the function of airway pressure sampling line 915 with the function of airway valve activation conductor 710. The latter function is implemented in the embodiment of bundled tube 2013 with wires 2016. The wires 2016 may activate the airway valve. In another embodiment, instead of using the volume of gas inside second lumen 2015 to communicate airway pressure, said second lumen 2015 could include additional wires (not shown) to carry the electrical signals from a pressure transducer at the airway. In this way, the second lumen would have more than two wires. Namely, two wires 2016 to activate the airway valve, and at least one wire to communicate the airway pressure signal electrically. In addition, bundled tube 2013 may also be embodied by two parallel tubes that are joined together longitudinally, with the lumens of each tube serving the functions described above. This embodiment viewed in cross-section is two circles touching or overlapping at one common point of their circumferences.

As described in the above paragraphs, lines 915, transducer 917, bundled tube 2013, port 1520 and port 1521 of airway valve 200 may constitute means to measure the airway pressure of the patient.

Typical airway pressures that are used as safety limits for mechanical ventilation during CPR are within the range of 60 to 80 centimeters of water. Protection to avoid exceeding these pressures is provided by a safety relief valve that opens at the mentioned range. However the safety relief valve occupies space and requires additional connecting pneumatic tubing and hardware, as is known in the art of medical ventilators. It would be ideal if this conventional safety relief valve hardware could be eliminated while preserving its function, so that a more compact and lightweight unit 700 can be built.

Another disadvantage of the typical relief valve values of 60 to 80 centimeters of water, which are currently used in conventional mechanical ventilators during CPR, is that they may cause gastric insufflation when the airway of the patient does not have an advanced airway device in place. For example, this may occur when an endotracheal tube is not present. In such cases of an unprotected airway, the sphincters of the esophagus may open with pressures much lower than those of the relief valves. Studies have reported esophageal sphincter opening in the range of 5 to 40 cm of water. One may wonder why are high relief values are used with such low sphincter opening values. The reason for the conventional high relief values of 60 to 80 cm of water is that the airway pressures observed during conventional ventilation in CPR are also high. During conventional intermittent positive pressure ventilations, high respiratory gas flow rates are necessary to deliver the recommended tidal volume (for example 700 mL) in a short period of time (1 second or so), as advised by current medical guidelines. High flow rates give rise to high airway pressures. Moreover, airway pressures tend to be high in conventional CPR because the compressions and ventilations may not be synchronized. As such, compression of the chest may coincide with an inspiratory ventilation, which yields high airway pressures. In order to achieve the ventilation at the tidal volume set by the rescuer, the manufacturers of conventional mechanical ventilators recommend setting the relief pressure to a high value of about 60 to 80 cm of water. If it is set lower, the relief valve will open and the inspiratory gas will be exhausted to the ambient air instead of entering the patient. Because of this undesirable compromise of needing to comply with the set tidal volume, but having to do so while tolerating high airway pressures, gastric insufflation is very common in CPR situations. Gastric insufflation brings complications such as vomiting and pulmonary aspiration that result when the patient's stomach is distended. Thus, it would be desirable to ventilate the patient during CPR with a lower relief valve value.

With the following invention embodiment, it is possible to obtain such lower relief value (reducing gastric insufflation) and also eliminate relief valve hardware without compromising ventilation. This can be done by taking advantage of this invention's use of lower-than-conventional tidal volumes, delivered according to the sequences of FIG. 5 and FIG. 11. The discovery that lower tidal volumes,—near or below the dead space volume—, can be used with this invention was made by analyzing data from animal tests. In one such test, a 35.5 Kg pig received CPR according to the invention's sequence of FIG. 5, and was adequately ventilated with a tidal volume of 80 mL (which corresponds to 2.2 mL/Kg). Airway pressures were less than 10 cm of water, and arterial blood gases were near normal.

The second aspect enabling a low relief value ventilation system, and advantageously eliminating relief valve hardware, includes choosing a low spring constant of spring 1509 (FIG. 20B) so as to enable a lower relief airway pressure, while having the benefits of the inventive sequences of FIG. 5 and FIG. 11. When said lower pressure is reached, it will push against sealing surface 1501 and open the valve 200. A spring constant corresponding to a relief pressure of 10 to 40 cm of water can be chosen for spring 1509, for example. With this choice of spring constant, and by virtue of the low airway pressures inherent to the sequences of FIG. 5 and FIG. 11, it is possible to combine the functions of two valves (the invention's airway valve 200, and the conventionally mandated safety relief valve, not shown) and simplify hardware.

Figure 20B:
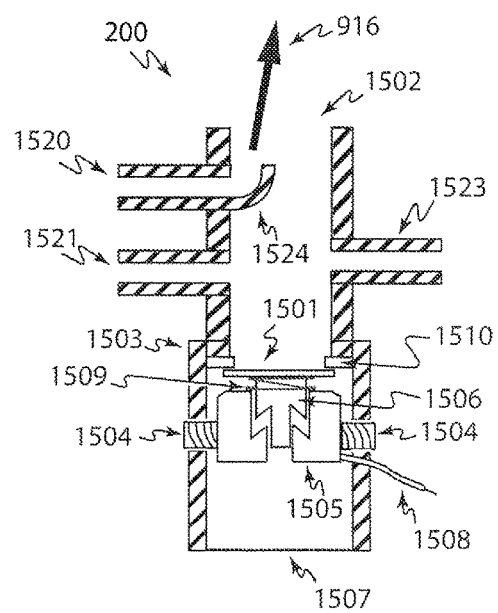
FIG. 20B shows an embodiment of an inventive airway valve of the present invention.
Figure 20C:
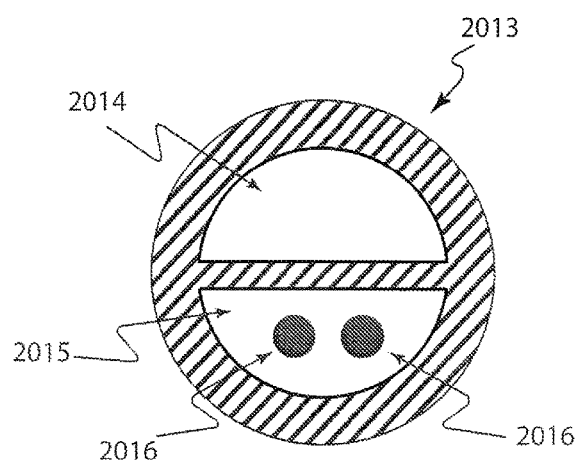
FIG. 20C shows an embodiment of an inventive bundled tube of the present invention for delivering ventilation to a patient and also monitoring the patient's airway pressure.

Airway valve 200 of FIG. 20B can be advantageously used to measure expiratory flow and thus the expired tidal volume. When solenoid 1505 is activated, airway valve 200 is thus open. If in that condition respiratory gases flow from the space of patient proximal end 1502 towards the space of patient distal end 1507, a pressure differential will occur between said two spaces. This is because solenoid 1505 and sealing surface 1501 present a resistance to flow through the valve 200. By monitoring the airway pressure through port 1521 as described previously, and measuring the ambient pressure (for example, with a pressure transducer in unit 700, the transducer coupled to the ambient), control unit 704 can determine the magnitude of flow of respiratory gases that are exiting the patient. This is possible because patient distal end 1507 is normally at ambient pressure, as it is exposed to the environment. By integrating said flow magnitude over time, control unit 704 can determine the expired tidal volume, which in the absence of leaks is equivalent to the delivered tidal volume. Control unit 704 may advantageously use the tidal volume information to control the quantity of oxygen delivered via valve 906, (with conventional control methods known in engineering arts), or it may report it to the rescuer via a display on unit 700, or do both functions of control and report. If during oxygen injection, unit 700 measures the pressure of oxygen present at valve 906 when it is open, then a pressure differential will develop across valve 906 and pressure port 1521, that is, across the resistance presented by line 914, enabling the determination of the magnitude of inspiratory flow and thus the inspired tidal volume, as was done before for the expired case. Since control unit 704 has both inspired tidal volume and expired tidal volume, a leak detector can be implemented by comparing them. If the expired tidal volume is less than the inspired tidal volume, a leak in the seal of the airway is present and an alarm can be given to the rescuer. The techniques of measurement of flow based on pressure differentials are known to those skilled in the art of medical ventilation.

Turning now to another aspect of ventilation, it is common during resuscitation to monitor exhaled carbon dioxide of the patient. This is typically done with intermittent positive pressure ventilation and measurement of the end tidal carbon dioxide (ETCO2). As is well known in the art of intensive care and emergency patient monitoring, a mainstream carbon dioxide sensor, or a side-stream carbon dioxide sampling line can be coupled to the airway of the patient. For example, if using an infrared mainstream sensor, it can be disposed between airway valve 200 and endotracheal tube 712. To minimize dead space, such sensor can preferably be coupled to the patient distal end 1502 of the valve shown in FIG. 20B. If using a side-stream sampling sensor, its corresponding sampling tube can be connected to a carbon dioxide sampling port 1523 disposed near the patient-proximal end 1502 of the airway valve 200, as shown in FIG. 20B.

Either of these carbon dioxide monitoring methods (mainstream or side-stream sampling) may be used with airway valve 200 of this invention. In order to enable the benefits of circulation and perfusion of this invention, smaller than currently conventional tidal volumes are used by the invention, as explained before. When low tidal volumes are used, the end tidal carbon dioxide sample of the expired gas may not reflect the alveolar carbon dioxide partial pressure, as is known in mechanical ventilation arts. Larger tidal volumes (e.g., 500-1000 mL) are needed for accurate measurement. To maintain the enhanced perfusion realized by the invention and yet allow effective carbon dioxide monitoring, the control unit 704 can periodically command a larger injection of oxygen (for example, by prolonging the duration of state 405 in FIG. 5 or FIG. 11 to approximately one to two seconds, thereby injecting a greater oxygen volume into the patient's lungs).

Because such larger positive pressure ventilation could inhibit circulation, the frequency of said deeper ventilations should be kept low. As such, the deeper carbon dioxide sampling ventilations in this aspect of the invention are done infrequently as compared to current practice, which is every 6 seconds when an advanced airway is in place, or every 18 seconds when there is none. Although any frequency may be used without departing from the scope of the invention, this invention preferably uses a deep ventilation sample every minute, or at a most frequent interval, every 15 seconds. However, any interval longer than current practice would provide improvement in circulation, especially when also using the inventive sequences described in this document. Alternatively, manual sampling activation could be implemented so that a rescuer could press a button on unit 700 and thereby initiate a larger, sampling ventilation.

Small carbon dioxide monitors, available now or in the future, could be advantageously included within unit 700, to reduce clutter and further integrate the equipment used in rescue situations. One example of such a current monitor is the side-stream type, which continuously draws a small flow (50-250 mL/minute) of respiratory gas from the airway of the patient to measure the carbon dioxide level, as is known to those skilled in the art of medical ventilation. In one embodiment of the invention, a plastic tube line (not shown) would connect airway valve port 1523 to the carbon dioxide monitor in unit 700. As a further improvement, that function could be implemented as part of bundled lumen tube 2013, which could have a third lumen (not shown). This would reduce further clutter in the rescue scene. In yet another improvement of automation, control unit 704 may then use the information of carbon dioxide levels to adjust ventilation tidal volumes, as is known in the art. For example, if high levels of carbon dioxide are monitored, control unit 704 may increase the oxygen delivered, as explained previously (greater injection flow or greater injection duration). Alternatively, an external carbon dioxide monitor could wirelessly or through a cable transmit the carbon dioxide levels to control unit 704, which would then adjust ventilation as described above, depending on the information received.

As will be evident to those skilled in the art, the above invention embodiments that referenced the sequences of FIG. 5 and FIG. 11, can also be embodied with the sequences the FIG. 18.

Although various representative embodiments of this invention have been described above with a certain degree of particularity, those skilled in the art could make numerous alterations to the disclosed embodiments without departing from the spirit or scope of the inventive subject matter set forth in the specification and claims. Joinder references (e.g. attached, adhered, joined) are to be construed broadly and may include intermediate members between a connection of elements and relative movement between elements. As such, joinder references do not necessarily infer that two elements are directly connected and in fixed relation to each other. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

The invention claimed is:

1. An apparatus comprising:
   sealing means to control an airway of a patient, said patient further having lungs, a chest, and an anterior to posterior distance;
   an airway valve that in combination with said sealing means is configured to open and close said airway;
   means to actuate said airway valve;
   an oxygen source to deliver oxygen to said patient;
   an oxygen valve to control oxygen flow;
   an oxygen valve actuator;
   means to deliver mechanical compressions to said chest;
   a control unit coupled to said airway valve actuating means, said oxygen valve actuator, and said mechanical compression delivery means;
   said control unit configured to actuate said airway valve, said mechanical compression delivery means, and said oxygen valve to deliver oxygen quantities based on said anterior to posterior distance.

2. The apparatus of claim 1 wherein said apparatus is further configured to measure said anterior to posterior distance.

3. The apparatus of claim 1 wherein said control unit is configured to calculate a tidal volume from said anterior to posterior distance.

4. The apparatus of claim 1 wherein said control unit is further configured to actuate said airway valve, said mechanical compression delivery means, and said oxygen valve to effect a sequence of states consisting of:
   compressed chest with closed airway;
   decompressed chest with closed airway;
   compressed chest with open airway to ventilate respiratory gas out of said lungs;
   decompressed chest with closed airway; and
   decompressed chest with said oxygen valve open to ventilate oxygen into said lungs.

5. The apparatus of claim 1 further comprising sensor means to sense compressions on said chest and wherein said compressions and said decompressions of said sequence are sensed by said sensor means such that the sequence consists of:
   closed airway during a sensed compression;
   closed airway during a sensed decompression;
   open airway to ventilate respiratory gas out of said lungs during a sensed compression;
   closed airway during a sensed decompression; and
   open oxygen valve to ventilate oxygen into the lungs of the patient during a sensed decompression.

6. The apparatus of claim 1 wherein said control unit is further configured to actuate said airway valve, said mechanical compression delivery means, and said oxygen valve to effect a sequence of states consisting of:
   compressed chest with closed airway;
   compressed chest with open airway to ventilate respiratory gas out of said lungs;
   decompressed chest with closed airway; and
   decompressed chest with said oxygen valve open to ventilate oxygen into said lungs.

7. The apparatus of claim 1 further comprising sensor means to sense compressions on said chest and wherein said compressions and said decompressions of said sequence are sensed by said sensor means such that the sequence consists of:
  closed airway during a sensed compression;
  open airway to ventilate respiratory gas out of said lungs during a sensed compression;
  closed airway during a sensed decompression; and
  open oxygen valve to ventilate oxygen into said lungs during a sensed decompression.

8. The apparatus of claim 1 wherein said control unit is further configured to actuate said airway valve, said mechanical compression delivery means, and said oxygen valve to effect a sequence of states consisting of:
  decompressed chest and open oxygen valve to ventilate oxygen into said lungs;
  compressed chest with closed airway; and
  compressed chest with open airway to let respiratory gas out of said lungs.

9. The apparatus of claim 1 wherein said control unit is further configured to actuate said airway valve, said mechanical compression delivery means, and said oxygen valve to effect a sequence of states consisting of:
  decompressed chest and open oxygen valve to ventilate oxygen into said lungs;
  compressed chest with closed airway;
  compressed chest with open airway to let respiratory gas out of said lungs;
  decompressed chest with closed airway;
  compressed chest with closed airway; and
  compressed chest with open airway to let respiratory gas out of said lungs.

10. The apparatus of claim 1 further comprising sensor means to sense compressions on said chest and wherein said compressions and said decompressions of said sequence are sensed by said sensor means such that the sequence consists of:
  open oxygen valve to ventilate oxygen into said lungs during a sensed decompression;
  closed airway during a sensed compression;
  open airway to let respiratory gas out of said lungs during a sensed compression;
  closed airway during a sensed decompression closed airway during a sensed compression; and
  open airway to let respiratory gas out of said lungs during a sensed compression.

11. An apparatus comprising:
  sealing means to control the airway of a patient, said patient further having a chest, lungs, airway pressure, and anterior to posterior distance;
  an airway valve that in combination with said sealing means is configured to open and close said airway;
  means to actuate said airway valve;
  an oxygen source to deliver oxygen to said patient;
  an oxygen valve to control oxygen flow;
  an oxygen valve actuator;
  means to deliver mechanical compressions to said chest;
  means to monitor said airway pressure;
  a control unit coupled to said airway valve actuating means, said oxygen valve actuator; said airway pressure monitoring means, and said mechanical compression delivery means;
  said control unit configured to:
    actuate said airway valve, said mechanical compression delivery means, and said oxygen valve to deliver oxygen quantities based on said anterior to posterior distance; and
    automatically adjust said quantities based on said airway pressure.

12. The apparatus of claim 11 further comprising at least one tube having a first lumen and a second lumen wherein:
  said first lumen provides oxygen flow to said patient; and
  said second lumen comprises said means to monitor said airway pressure.

13. The apparatus of claim 12 wherein said second lumen further comprises wires and wherein said wires are configured to perform functions consisting of airway valve activation conduction, communication of airway pressure, carry electric signals to a pressure transducer, and combinations thereof.

14. The apparatus of claim 11 wherein said control unit is further configured to actuate said airway valve, said mechanical compression delivery means, and said oxygen valve to effect a sequence of states consisting of:
  compressed chest with closed airway;
  decompressed chest with closed airway;
  compressed chest with open airway to ventilate respiratory gas out of said lungs;
  decompressed chest with closed airway; and
  decompressed chest with said oxygen valve open to ventilate oxygen into said lungs.

15. The apparatus of claim 11 further comprising sensor means to sense compressions on said chest and wherein said compressions and said decompressions of said sequence are sensed by said sensor means such that the sequence consists of:
  closed airway during a sensed compression;
  closed airway during a sensed decompression;
  open airway to ventilate respiratory gas out of said lungs during a sensed compression;
  closed airway during a sensed decompression; and
  open oxygen valve to ventilate oxygen into the lungs of the patient during a sensed decompression.

16. The apparatus of claim 11 wherein said control unit is further configured to actuate said airway valve, said mechanical compression delivery means, and said oxygen valve to effect a sequence of states consisting of:
  compressed chest with closed airway;
  compressed chest with open airway to ventilate respiratory gas out of said lungs;
  decompressed chest with closed airway; and
  decompressed chest with said oxygen valve open to ventilate oxygen into said lungs.

17. The apparatus of claim 11 further comprising sensor means to sense compressions on said chest and wherein said compressions and said decompressions of said sequence are sensed by said sensor means such that the sequence consists of:
  closed airway during a sensed compression;
  open airway to ventilate respiratory gas out of said lungs during a sensed compression;
  closed airway during a sensed decompression; and
  open oxygen valve to ventilate oxygen into said lungs during a sensed decompression.

18. The apparatus of claim 11 wherein said control unit is further configured to actuate said airway valve, said mechanical compression delivery means, and said oxygen valve to effect a sequence of states consisting of:
  decompressed chest and open oxygen valve to ventilate oxygen into said lungs;
  compressed chest with closed airway; and
  compressed chest with open airway to let respiratory gas out of said lungs.

19. The apparatus of claim 11 wherein said control unit is further configured to actuate said airway valve, said mechanical compression delivery means, and said oxygen valve to effect a sequence of states consisting of:
- decompressed chest and open oxygen valve to ventilate oxygen into said lungs;
- compressed chest with closed airway;
- compressed chest with open airway to let respiratory gas out of said lungs;
- decompressed chest with closed airway;
- compressed chest with closed airway; and
- compressed chest with open airway to let respiratory gas out of said lungs.

20. The apparatus of claim 11 further comprising sensor means to sense compressions on said chest and wherein said compression and said decompressions of said sequence are sensed by said sensor means such that the sequence consists of:
- open oxygen valve to ventilate oxygen into said lungs during a sensed decompression;
- closed airway during a sensed compression;
- open airway to let respiratory gas out of said lungs during a sensed compression;
- closed airway during a sensed decompression;
- closed airway during a sensed compression; and
- open airway to let respiratory gas out of said lungs during a sensed compression.

21. An apparatus comprising:
- sealing means to control the airway of a patient;
- an airway valve that in combination with said sealing means is configured to open and close said airway;
- means to actuate said airway valve;
- an oxygen source to deliver oxygen to said patient;
- an oxygen valve to control oxygen flow;
- an oxygen valve actuator;
- means to deliver mechanical compressions to said patient's chest;
- means to monitor exhaled carbon dioxide of the patient;
- a control unit coupled to said airway valve actuating means, said oxygen valve actuator, said mechanical compression delivery means, and said carbon dioxide monitoring means;
- said control unit configured to effect sequences of chest compressions and oxygen ventilations, said ventilations comprising first ventilations with a tidal volume of less than 500 milliliters, and second ventilations with a tidal volume of at least 500 milliliters, and wherein the control unit is configured to sample the end tidal carbon dioxide from the exhaled carbon dioxide using said second ventilations.

22. The apparatus of claim 21 wherein said second ventilations are delivered no more often than once every fifteen seconds.

23. The apparatus of claim 22 wherein said second ventilations are delivered at intervals between once every fifteen seconds to once every minute.

24. A cardio-pulmonary resuscitation apparatus comprising:
- an airway valve including means to provide a safety relief when a pressure within said valve is great enough to actuate said safety relief, said safety relief comprising a spring and a sealing surface wherein said pressure presses against said sealing surface to actuate said spring, said spring having a spring constant corresponding to a relief pressure less than forty centimeters of water;
- sealing means to control the airway of a patient;
- said airway valve including
- an oxygen port connected to an oxygen source having an oxygen valve and means to actuate said oxygen valve, said oxygen port angled toward said airway;
- a pressure sampling port for monitoring a pressure of said airway by an airway pressure monitor means;
- a carbon dioxide sampling port for monitoring exhaled carbon dioxide of said patient by a carbon dioxide monitoring means;
- means to actuate said airway valve;
- means to deliver mechanical compressions to the chest of said patient;
- a control unit coupled to said airway valve actuating means, said oxygen valve actuator, said airway pressure monitoring means, said carbon dioxide monitoring means, and said mechanical compression delivery means.

25. The cardio-pulmonary resuscitation apparatus of claim 24 wherein said relief pressure is between ten centimeters of water and forty centimeters of water.

* * * * *